(12) United States Patent
Xue et al.

(10) Patent No.: US 12,290,262 B2
(45) Date of Patent: May 6, 2025

(54) STAPLER

(71) Applicants: JIANGSU YUNZHONG MEDICAL TECHNOLOGY CO., LTD., Wuxi (CN); Jianxin Xue, Wuxi (CN)

(72) Inventors: Jianxin Xue, Wuxi (CN); Yun Guo, Wuxi (CN); Zengjun Wang, Wuxi (CN); Yong Feng, Wuxi (CN); Chunmei Chen, Wuxi (CN); Xiao Li, Wuxi (CN); Kai Zhu, Wuxi (CN)

(73) Assignees: Jianxin Xue, Wuxi (CN); JIANGSU YUNZHONG MEDICAL TECHNOLOGY CO., LTD., Wuxi (CN)

( * ) Notice: Subject to any disclaimer, the term of this patent is extended or adjusted under 35 U.S.C. 154(b) by 13 days.

(21) Appl. No.: 18/260,756

(22) PCT Filed: Jan. 7, 2022

(86) PCT No.: PCT/CN2022/070612
§ 371 (c)(1),
(2) Date: Jul. 7, 2023

(87) PCT Pub. No.: WO2022/148407
PCT Pub. Date: Jul. 14, 2022

(65) Prior Publication Data
US 2024/0050094 A1 Feb. 15, 2024

(30) Foreign Application Priority Data
Jan. 8, 2021 (CN) .......................... 202110022419.7

(51) Int. Cl.
*A61B 17/115* (2006.01)

(52) U.S. Cl.
CPC ................. *A61B 17/115* (2013.01)

(58) Field of Classification Search
CPC .................................................. A61B 17/1152
(Continued)

(56) References Cited

U.S. PATENT DOCUMENTS

| 3,606,888 A * | 9/1971 | Wilkinson ......... A61B 17/1152 227/19 |
| 6,769,590 B2 * | 8/2004 | Vresh .................. A61B 17/1114 227/176.1 |

(Continued)

FOREIGN PATENT DOCUMENTS

| CN | 1868412 A | 11/2006 |
| CN | 104840228 A | 8/2015 |

(Continued)

OTHER PUBLICATIONS

International Search Report dated Mar. 22, 2022 for International Application No. PCT/CN2022/070612.

*Primary Examiner* — Joshua G Kotis
*Assistant Examiner* — Patrick B Fry

(57) ABSTRACT

The present disclosure provides a stapler, including a shell, an ejector plate pin, a cartridge pin, an anvil pin, an unlocking pin, an ejector plate ring, a cartridge ring and an anvil ring, where the cartridge pin is between the ejector plate pin and the anvil pin; the ejector plate ring, the cartridge ring and the anvil ring all include a first half ring and a second half ring; hinged ends of the first half rings and the second half rings are rotatably connected, and fixed ends of the second half rings of the ejector plate ring, the cartridge ring and the anvil ring are connected to the front ends of the ejector plate pin, the cartridge pin and the anvil pin, respectively. The present disclosure adopts a brand-new concept of eversion anastomosis, and ensures the smoothness of a lumen after anastomosis.

20 Claims, 18 Drawing Sheets

(58) Field of Classification Search
USPC .................................................... 227/176.1
See application file for complete search history.

(56) References Cited

U.S. PATENT DOCUMENTS

| | | | |
|---|---|---|---|
| 2003/0222117 A1 | 12/2003 | Orban, III | |
| 2005/0067454 A1 | 3/2005 | Vresh | |
| 2020/0205834 A1* | 7/2020 | Drochner | ............... A61B 17/11 |

FOREIGN PATENT DOCUMENTS

| | | | | |
|---|---|---|---|---|
| CN | 105125249 A | | 12/2015 | |
| CN | 111789649 A | | 10/2020 | |
| CN | 111870298 A | * | 11/2020 | ......... A61B 17/1114 |
| EP | 2090251 A2 | | 8/2009 | |

* cited by examiner

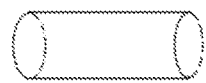
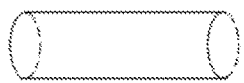
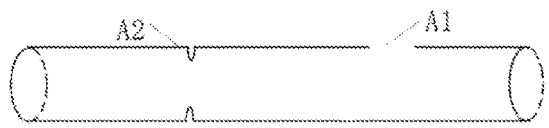
FIG. 1
FIG. 2
FIG. 3
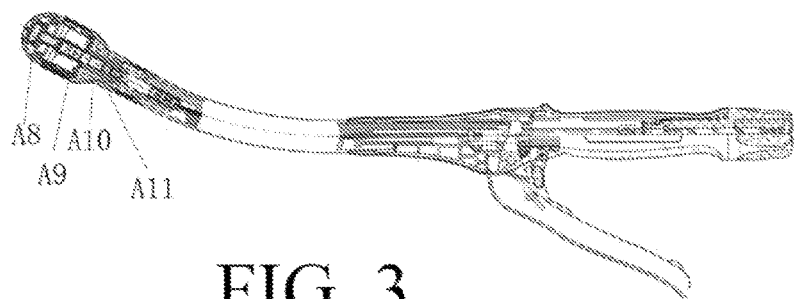
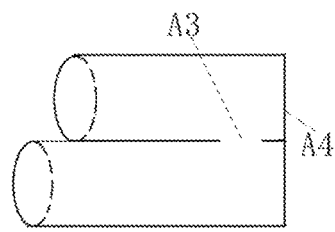
FIG. 4

STAPLER

TECHNICAL FIELD

The present disclosure relates to the field of medical appliances, and relates to a stapler, particularly to a circular cutting stapler for extraluminal use.

BACKGROUND

Due to the development of modern science and technology, a cutting stapler has emerged and replaced traditional manual stitching. A cutting stapler has the advantages of fast and reliable anastomosis, fewer postoperative complications, and the like. The working principle of a cutting stapler is similar to that of a book stapler, that is, anastomosing and cutting tissues and organs with titanium screws and blades. The existing cutting staplers are mainly used for cutting and anastomosing skin, digestive tracts, blood vessels, lungs, and the like, and are applicable to laparoscopic and open surgeries. The repair and reconstruction of many lumen-like internal structures (e.g., urinary tracts including urethra, bladder urethra, ureter bladder and ureter; intestines; and blood vessels) currently are mainly conducted by manual suture anastomosis and the use of an intraluminal circular stapler or multiple linear cutting staplers for anastomosis in clinical practice. An intraluminal circular stapler is suitable for end-to-end or end-to-side anastomosis, but requires an additional stoma and requires secondary anastomosis of the stoma, which artificially increases the difficulty, cost, and potential complications of a surgery. In addition, an anastomotic nail is located in tissue and organ cavities, which is not suitable for many tissues and organs (e.g., blood vessels and ureters) that require eversion anastomosis. An anastomotic nail located in a cavity may also cause postoperative complications such as stenosis and obstruction. The use of multiple linear cutting staplers increases the difficulty of anastomosis surgery, and the junction of anastomotic nails is prone to postoperative tissue necrosis of anastomotic stoma, fistula, bleeding, or stenosis and obstruction. At the same time, the use of multiple cartridges greatly increases the cost of surgery.

The following is a detailed description of the problems existing in the prior art in conjunction with the accompanying drawings.

As shown in FIG. 1, two segments of lumens need to be sutured end-to-end during surgery.

Combined with FIG. 2, FIG. 3, and FIG. 5, the commonly used inversion anastomosis is shown, where, firstly, a wound A1 is created on the right segment of the lumen, and a stapler with a bent end shown in FIG. 3 is extended into the lumen. The operating handle of the stapler is outside the lumen. The two broken ends of the lumen are pulled between a circular anvil A8 and a circular cartridge A10, and an ejector seat A11 is pushed to strike an anastomotic nail in the circular cartridge A10 to nail the two broken ends of the lumen together. The excess tissue is excised by a circular blade A9, forming a circular inversion sutured lumen tissue A2 as shown in FIG. 2. Then the stapler is removed from the lumen through the wound A1, and the wound A1 is sutured by a stapler shown in FIG. 5. This suture method has at least three drawbacks: (1) The inversion sutured lumen tissue A2 formed by inversion anastomosis protrudes from the inner wall of the lumen, which can easily cause many complications such as stenosis and obstruction after surgery. (2) The wound A1 needs to be created on the lumen and anastomosed, which is an additional incision required for the surgery, increases the difficulty of the surgery and brings unnecessary injury to the patient. (3) The use of two types of staplers greatly increases the cost of the surgery.

FIG. 4 and FIG. 5 show a second anastomosis method, where the right segment of lumen in FIG. 1 is pulled, and the two broken ends are placed side by side, so that the outer walls of the two segments of lumens are attached together. Then, the two segments of lumens are anastomosed side-to-side using the linear stapler shown in FIG. 5, that is, the walls of the two segments of lumens that are attached together are placed between a cartridge A6 and an anvil A7, and the lumen walls are anastomosed by striking anastomotic nails in the cartridge A6. Then a stoma A3 is created at the anastomotic site, and finally the ends of the two segments of lumens are anastomosed using the linear stapler shown in FIG. 5. Then the fistula A3 becomes the connecting port between the two segments of lumens. This method of anastomosis has at least three drawbacks: (1) The original direction of one segment of the lumen needs to be changed, and the lumen is pulled by external force, which will cause damage to the lumen. (2) After anastomosis, the flowing content in the lumen moves through the fistula A3, and forms a 90 degree turn inside the lumen, resulting in unsmooth flow and probably obstruction. (3) Anastomosis needs to be conducted twice or more times, greatly increasing the cost and difficulty of the surgery.

FIG. 6 shows an eversion suture method, where the two broken ends are everted to form a circular eversion sutured lumen tissue A5. The advantages of this method are obvious, as the suture site is outside the lumen and cannot cause postoperative complications such as stenosis or obstruction. However, in current surgeries, this method is limited to manual suture and cannot use staplers. Referring to FIG. 3, if the broken ends of the two segments of lumens are everted on the circular anvil A8 and the circular cartridge A10 and then sutured, the stapler cannot be removed from the sutured lumen. To achieve eversion anastomosis using a stapler, the invention patent with the application number 201510282427X provides an extraluminal anastomosis method, where a circular structure of a cartridge and a base is cut through using scissors after a lumen is sutured, thereby removing the cartridge and the base. However, this method is only an idea without detailed structural features provided. There are at least four reasons why this method cannot be applied in clinical practice: (1) The surgical space is very small, making it difficult to insert a pair of scissors between the tissue and an anastomosis ring after suturing to cut off the circular structure. (2) When the circular structure is cut by scissors, external force needs to be applied, so that improper operation may cause secondary damage to the lumen tissue, and even pull the lumen apart. (3) A material that is easy to be cut and damaged by scissors is inevitably not rigid enough to form sufficient anastomotic traction, and is also destructive to surgical scissors. (4) In the anastomosis method, an anvil ring is pulled to compress an anastomotic nail towards the near-end, and as the far-end situation cannot be observed during the surgery, tissue and organ tears may be caused.

SUMMARY

The objective of the present disclosure is to provide a stapler for achieving end-to-end eversion anastomosis, where after anastomosis, a circular structure can be opened to achieve automatic ring release, and the stapler can be removed from a lumen after anastomosis, greatly improving the success rate of anastomosis and reducing complications.

The stapler provided by the present disclosure includes a shell, as well as an ejector plate pin, a cartridge pin, an anvil pin, an unlocking pin, an ejector plate ring, a cartridge ring and an anvil ring, where the cartridge pin is between the ejector plate pin and the anvil pin; the ejector plate ring, the cartridge ring and the anvil ring all include a first half ring and a second half ring;

hinged ends of the first half rings and the second half rings are rotatably connected, and fixed ends of the second half rings of the ejector plate ring, the cartridge ring and the anvil ring are connected to the front ends of the ejector plate pin, the cartridge pin and the anvil pin, respectively; the rear end of the anvil pin is fixedly installed in the shell, and the rear ends of the ejector plate pin and the cartridge pin are movably installed in the shell and can move back and forth along the length direction of the pin bodies; and the ejector plate ring, the cartridge ring and the anvil ring are all provided with lock catches for locking the free ends of the first half rings to the fixed ends of the second half rings, and when the unlocking pin is pushed forward along the length direction of the pin body, the unlocking pin opens the lock catches.

Preferably, the lock catches include male buckles and female buckles, where the male buckles are arranged on the free ends of the first half rings, the female buckles are arranged on the fixed ends of the second half rings, and circular structures are formed when the male buckles are locked with the female buckles; unlocking columns perpendicular to the length direction of the pin body are arranged in the second half rings;

the unlocking pin is on the outer side of the anvil pin, the unlocking columns of the ejector plate ring, the cartridge ring and the anvil ring pass through and extend out of the anvil pin respectively, or the unlocking pin is arranged in the anvil pin, and the rear end of the unlocking pin is arranged outside the anvil pin, and the unlocking columns of the ejector plate ring, the cartridge ring and the anvil ring extend into the anvil pin respectively; the cartridge pin is provided with an avoidance slot for the unlocking column of the ejector plate pin to move along the length direction of the pin body, and the anvil pin is provided with an avoidance slot for the unlocking columns of the ejector plate pin and the cartridge pin to move along the length direction of the pin body; and when the unlocking pin is pushed forward, the unlocking pin pushes the unlocking columns to move away from the anvil pin, thereby unlocking the male buckles and female buckles through the unlocking columns.

Preferably, the male buckles are elastic arms, the female buckles are grooves, and the unlocking columns push the elastic arms out of the grooves to achieve unlocking.

Preferably, the free ends of the first half rings are provided with male buckle grooves, the male buckles are spheres arranged in the male buckle grooves through expansion springs, the female buckles are grooves, and the unlocking columns push the spheres out of the grooves to achieve unlocking.

Preferably, both the male buckles and the female buckles are hook-shaped, the hook-shaped male buckles and the hook-shaped female buckles are hooked to achieve locking, and the unlocking columns push the hook-shaped female buckles to achieve unlocking.

Preferably, the unlocking columns are sheathed with unlocking springs, and in the absence of external force from the unlocking pin, the unlocking springs cause the unlocking columns to reset, so as to avoid affecting the locking of the male buckles and the female buckles.

Preferably, a drive pin that can move back and forth is arranged in the shell, and the drive pin is connected to the rear end of the ejector plate pin; the front end of the drive pin is a double fork arm structure, the rear end of the cartridge pin is provided with a convex cartridge pin rear end protrusion, the cartridge pin rear end protrusion is in an accommodation cavity of the double fork arm structure, and the body of the cartridge pin penetrates from the gap between an upper extension and a lower extension of the double fork arm structure; the shell is also provided with a limiting button moving slot extending along the length direction of the pin body and a limiting button passing through the limiting button moving slot; the limiting button is provided with a limiting button end convex block which extends into the accommodation cavity; and the limiting button can move along the length direction thereof, and when the limiting button end convex block is between the rear wall of the accommodation cavity and the cartridge pin rear end protrusion, the drive pin can drive the cartridge pin to move forward.

Preferably, the rear end of the ejector plate pin is provided with a convex ejector plate pin rear end protrusion, the ejector plate pin rear end protrusion is in the accommodation cavity and in contact with the front wall and rear wall of the accommodation cavity, and the body of the ejector plate pin penetrates from the gap between the upper extension and the lower extension of the double fork arm structure; and a through hole for the limiting button to pass through is formed in the ejector plate pin rear end protrusion.

Preferably, at the rear end of the cartridge pin, cartridge pin elastic wings are arranged on the cartridge pin, and the cartridge pin elastic wings open towards the rear end; in front of the cartridge pin elastic wings, an unlocking press plate that can move back and forth along the cartridge pin is arranged on the cartridge pin; the front end of the shell is internally provided with a clamping groove that matches the cartridge pin elastic wings; when the unlocking press plate moves to the cartridge pin elastic wings, the cartridge pin elastic wings are retracted; and when the unlocking press plate moves away from the cartridge pin elastic wings towards the far-end, the cartridge pin elastic wings are clamped in the clamping groove.

Preferably, the shell is provided with an unlocking button moving slot extending along the length direction of the pin body, and also includes an unlocking button extending out of the shell from the unlocking button moving slot; and the inner end of the unlocking button is connected to the unlocking press plate.

Preferably, the inner end of the unlocking button is connected to the rear end of the unlocking pin, and the unlocking pin is connected to the unlocking press plate.

Preferably, a connecting pin is further included, guide columns are arranged along the length direction of the pin body in the shell, a sliding seat at the rear end of the connecting pin is slidably installed on the guide columns, and the front end of the connecting pin is connected to the rear end of the unlocking pin.

Preferably, on both sides of the sliding seat, the guide columns are sheathed with a first unlocking pin spring and a second unlocking pin spring, respectively.

Preferably, the cartridge pin elastic wings are arranged on the upper and lower surfaces of the cartridge pin, and the unlocking press plate is in a frame or "[" shape.

Preferably, the limiting button moving slot is provided with graduations.

Preferably, the shell is provided with an unlocking button moving slot extending along the length direction of the pin body, and also includes an unlocking button extending out of the shell from the unlocking button moving slot; and the rear end of the unlocking pin is connected to the inner end of the unlocking button.

Preferably, a connecting pin is further included, guide columns are arranged along the length direction of the pin body in the shell, a sliding seat at the rear end of the connecting pin is slidably installed on the guide columns, the front end of the connecting pin is connected to the rear end of the unlocking pin, and the inner end of the unlocking button is connected to the connecting pin.

Preferably, on both sides of the sliding seat, the guide columns are sheathed with a first unlocking pin spring and a second unlocking pin spring, respectively.

Preferably, the unlocking button moving slot is provided with graduations.

Preferably, a fixed handle is arranged at the rear end of the shell, an active handle is rotatably installed on the fixed handle, and the active handle is in front of the fixed handle; a pawl is rotatably installed at the upper end of the active handle, and the front end of the pawl rests against a spine at the bottom of the drive pin; and a reset button is installed at the rear end of the drive pin, a reset button moving slot extending along the length direction of the drive pin is arranged on the shell, and the reset button passes through the reset button moving slot.

Preferably, ram limiting columns are arranged on one or both sides of the drive pin, and the two ram limiting columns on the same side are arranged at both ends of the drive pin; a ram is arranged on one or both sides of the drive pin, and inclined kidney-shaped holes are formed at both ends of the ram; the kidney-shaped holes are high in the front and low at the back, and the corresponding ram limiting columns pass through the two kidney-shaped holes respectively; a traction spring is further included, the rear ends of the rams are connected to the reset button, the front end of the traction spring is installed on the drive pin, and the rear end of the traction spring is connected to the reset button; under the action of the traction spring, the bottom ends of the kidney-shaped holes of the rams are in contact with the ram limiting column; when the reset button is pulled back, the reset button first pulls the ram; and when the top ends of the kidney-shaped holes of the rams are in contact with the ram limiting column, the rams act on the pawl to separate the pawl from the spine, and the reset button pulls the rams and the drive pin to move backward together.

Preferably, a traction spring installation cavity is arranged on the drive pin, a traction spring installation column is arranged at the front end of the traction spring installation cavity, the traction spring is arranged in the traction spring installation cavity, and the front end of the traction spring is installed on the traction spring installation column.

Preferably, an installation plate arranged in the spring installation cavity is further included, the rear end of the installation plate is connected to the reset button, and the front end of the installation plate is connected to the rear end of the traction spring.

Preferably, the reset button moving slot is provided with graduations.

Preferably, a reset button shaft is further included, the reset button shaft passes through the reset button moving slot, the rear end of the ram, and a reset button installation hole at the rear end of the drive pin, the two reset buttons are installed at both ends of the reset button shaft, and the rear end of the traction spring is connected to the reset button shaft.

Preferably, a rotating shaft of the active handle is sheathed with a torsion spring to reset the active handle; and the rotating shaft of the pawl is sheathed with a torsion spring for causing the pawl to rest against the spine.

Preferably, an ejector ring protecting plate is arranged on the outer side of a fixed end of a second half ring of the ejector plate ring or on the ejector plate pin, and the ejector ring protecting plate extends towards a free end of a first half ring of the ejector plate ring.

Preferably, an anvil protecting plate is arranged on the outer side of a fixed end of a second half ring of the anvil ring or on the anvil pin, and the anvil protecting plate extends towards a free end of a first half ring of the anvil ring.

Preferably, the cartridge ring is provided with anastomotic nails arranged in a staggered manner in two layers.

Preferably, anastomotic nails are arranged at the connection between the first half ring and the second half ring near the cartridge ring.

Preferably, the ejector plate ring is provided with an ejector plate that matches the anastomotic nails, and a circular blade is arranged at the outer edge of the ejector plate.

Preferably, the ends of the first half ring and the second half ring are L-shaped.

Preferably, a ring installation seat is arranged at the fixed ends of the second half rings of the ejector plate ring, the cartridge ring and the anvil ring, and the ring installation seat is detachably connected to the front ends of the ejector plate pin, the cartridge pin and the anvil pin.

Preferably, the ends of the unlocking columns of the ejector plate ring, the cartridge ring and the anvil ring are connected through a connecting plate, and the unlocking pin pushes the connecting plate to push the unlocking column.

Preferably, the limiting button is sheathed with a detachable safety catch.

The present disclosure provides a brand-new eversion stapler with the following advantages: (1) a brand-new eversion anastomosis concept ensures the smoothness of a lumen after anastomosis, especially for the situations of blood vessels (not limited to blood vessels) where eversion rapid anastomosis is required but no suitable stapler is available in clinical practice; (2) a semi-automatic solution for the stapler is provided, the operation is similar to traditional staplers, and a detailed locked/unlocked ring structure is provided, making the anastomosis more convenient and efficient; (3) the shortcomings of end-to-end anastomosis in the prior art that requires an additional stoma and additional anastomosis is solved, not only reducing clinical costs, but also reducing anastomotic complications and shortening surgical time; (4) real scenes are simulated and a correction structure is provided for the situation that the stapler may need to be readjusted during a surgery due to incomplete alignment; and (5) anastomotic nails are outside the lumen after anastomosis, reducing complications related to the anastomotic nails, e.g., anastomotic stoma stenosis, anastomotic nail related bleeding, and lithogenesis.

BRIEF DESCRIPTION OF THE DRAWINGS

FIG. 1 is a schematic diagram of two segments of lumens to be anastomosed.

FIG. 2 is a schematic diagram of inversion anastomosis.

FIG. 3 is a schematic diagram of a stapler for inversion anastomosis.

FIG. 4 is a schematic diagram of a luminal anastomosis method II.

Figure 5:
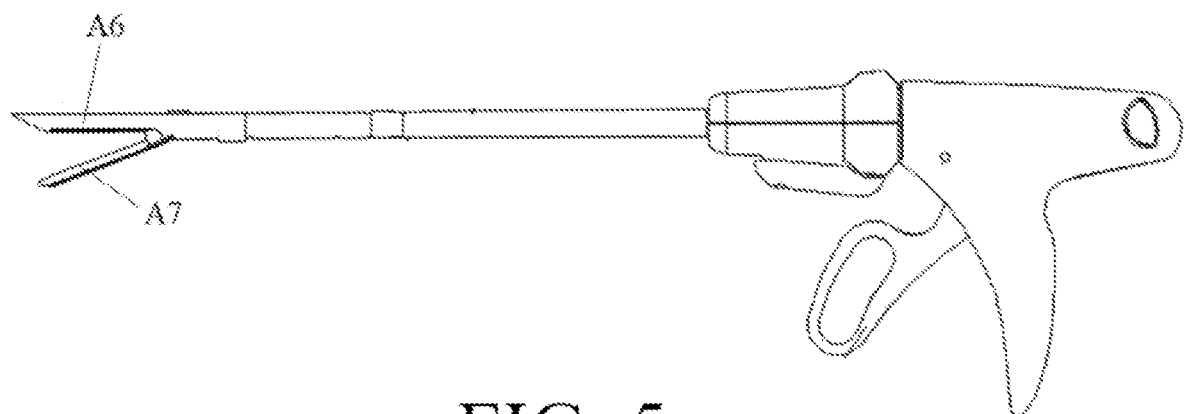
FIG. 5 is a schematic diagram of a stapler for external anastomosis.
Figure 6:
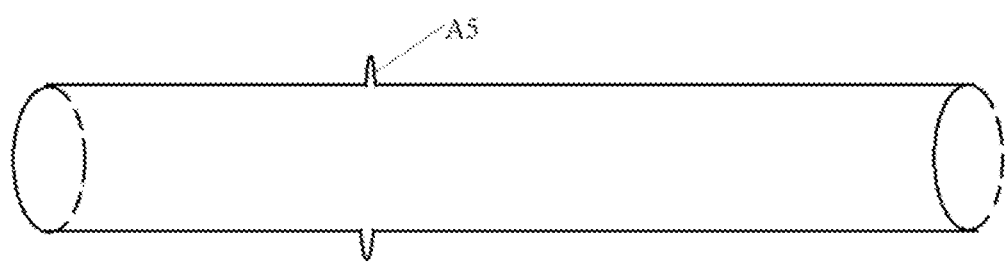
FIG. 6 is a schematic diagram of eversion anastomosis.

In the figures: A1—wound, A2—inversion sutured lumen tissue, A3—stoma, A4—end sutured lumen tissue, A5—eversion sutured lumen tissue, A6—cartridge, A7—anvil, A8—circular anvil, A9—circular blade, A10—circular cartridge, A11—ejector seat;

1—anvil ring, 101—anvil protecting plate, 102—connecting hinge, 103—first half ring, 104—second half ring;

2—cartridge ring, 201—anastomotic nail, 202—connecting hinge, 203—first half ring, 204—second half ring, 205—avoidance slot, 206—ring installation seat;

3—ejector plate ring, 301—circular blade, 302—ejector ring protecting plate, 303—connecting hinge, 304—ejector plate;

4—limiting button, 401—limiting button groove, 402—limiting button operating part; 403—limiting button end convex block;

5—drive pin, 501—spine, 502—upper extension, 503—ram limiting column, 504—lower extension, 505—reset button installation hole, 506—traction spring installation column, 507—traction spring installation cavity, 508—accommodation cavity, 510—installation plate;

6—ram, 601—kidney-shaped hole, 602—ram installation hole;

7—reset button, 701—traction spring, 702—reset button shaft;

8—active handle, 802—fixed nut, 803—reset spring;

9—anvil pin lock catch, 901—male buckle, 902—female buckle, 903—unlocking spring, 904—unlocking column;

10—cartridge pin lock catch, 1001—male buckle, 1002—female buckle, 1003—unlocking spring, 1004—unlocking column, 1005—expansion spring, 1006—male buckle groove, 1007—rotating shaft hole;

11—ejector plate pin lock catch, 1101—male buckle, 1102—female buckle, 1103—unlocking spring, 1104—unlocking column;

12—unlocking pin, 1201—unlocking press plate, 1202—connecting pin, 1203—sliding seat, 1204—first unlocking pin spring, 1205—guide column, 1206—second unlocking pin spring;

13—unlocking button, 1301—spring column, 1302—sliding seat, 1303—connecting pin, 14—pawl; 15—ejector plate pin, 1501—ejector plate pin rear end protrusion, 1502—avoidance hole; 16—cartridge pin, 1601—cartridge pin elastic wings, 1602—cartridge pin rear end protrusion, 1603—pushing surface;

17—anvil pin, 1701—unlocking pin through hole, 18—broken ends of the intestine; 19—shell, 1901—fixed handle, 1902—reset button moving slot, 1903—limiting button moving slot, 1904—unlocking button moving slot, 1905—clamping groove.

DETAILED DESCRIPTION

The following is a detailed description of the technical solution of the present disclosure in conjunction with FIGS. 7-30.

For clarity, the directional terms used in the accompanying drawings and the following description are relative to an operator holding a stapler handle horizontally with his/her right hand, where a fixed handle is located in the part of the right hand between the thumb and the index finger and an active handle is held by four fingers except for the thumb. Specifically, the terms "near" and "behind" refer to positions close to the operator, while the terms "far" and "front" refer to positions far away from the operator. The term "left" refers to the left side of the operator, while the term "right" refers to the right side of the operator. The term "up" refers to the direction opposite to gravity, while the term "down" refers to the direction of gravity. Other directional terms can be understood based on the accompanying drawings and the following description.

The circular cutting stapler for extraluminal use provided by the present disclosure includes an operation assembly, an extension assembly, and an execution assembly.

The operation assembly includes a stapler body, a handle trigger assembly, and an opening and closing assembly.

Figure 7:
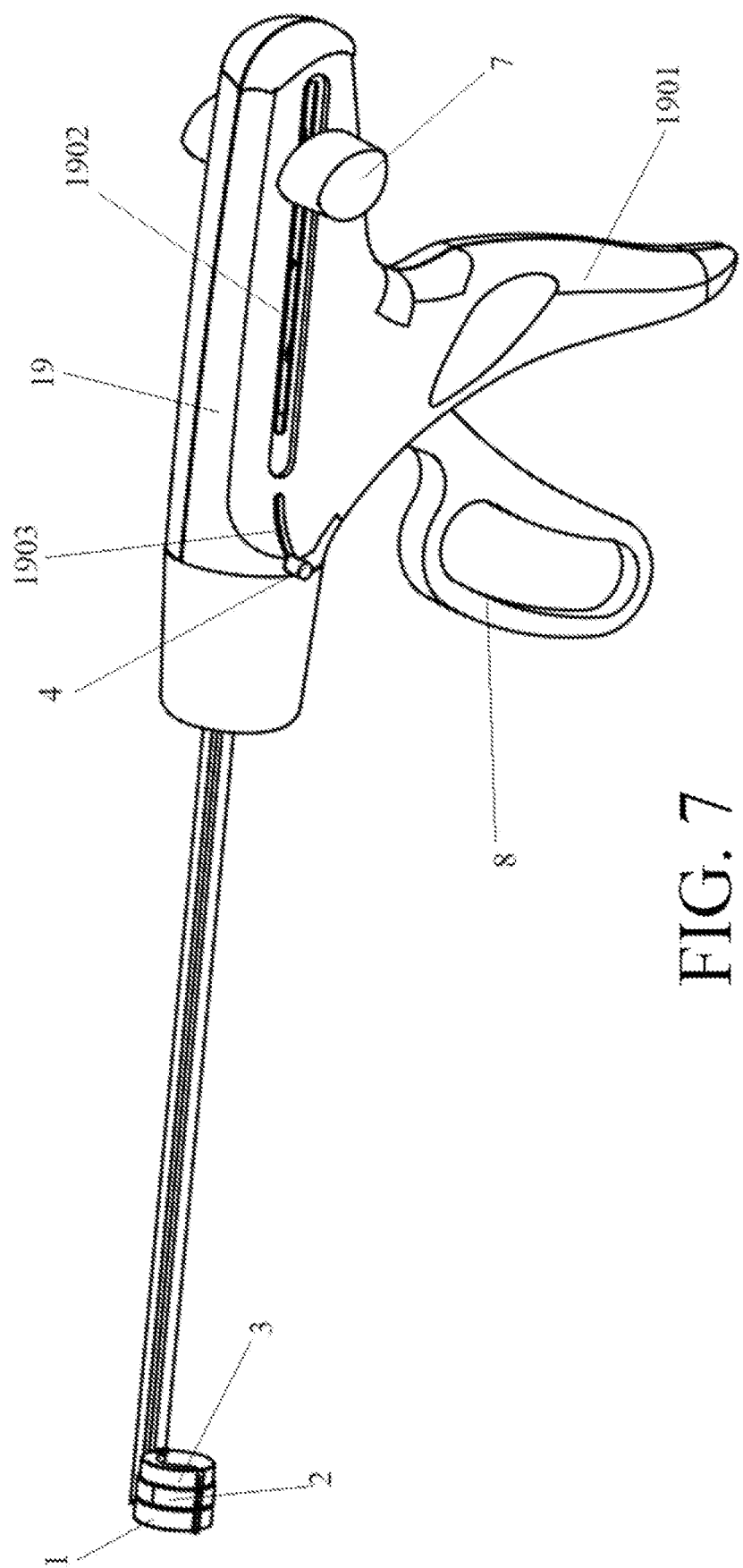
FIG. 7 is a three-dimensional view of the present disclosure (left view).
Figure 8:
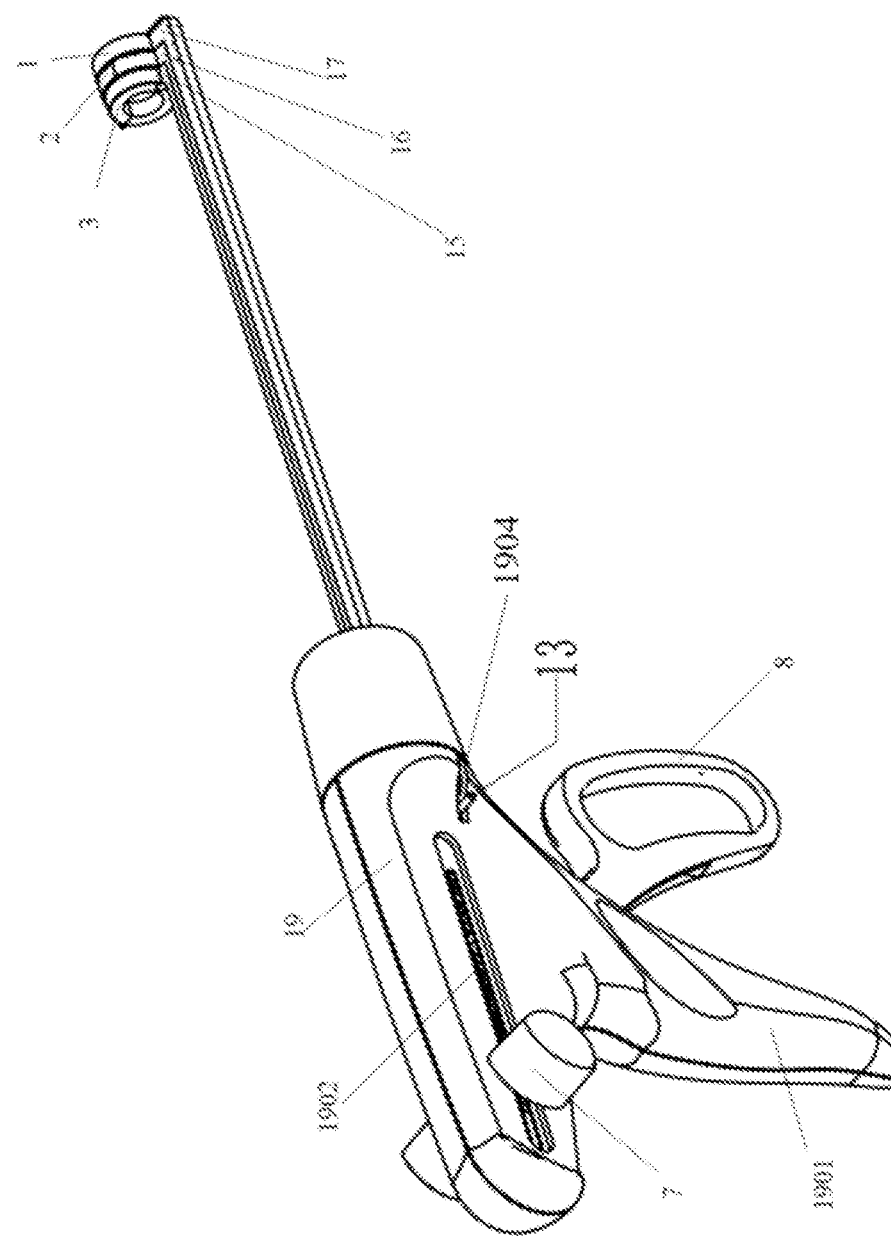
FIG. 8 is a three-dimensional view of the present disclosure (right view).
Figure 9:
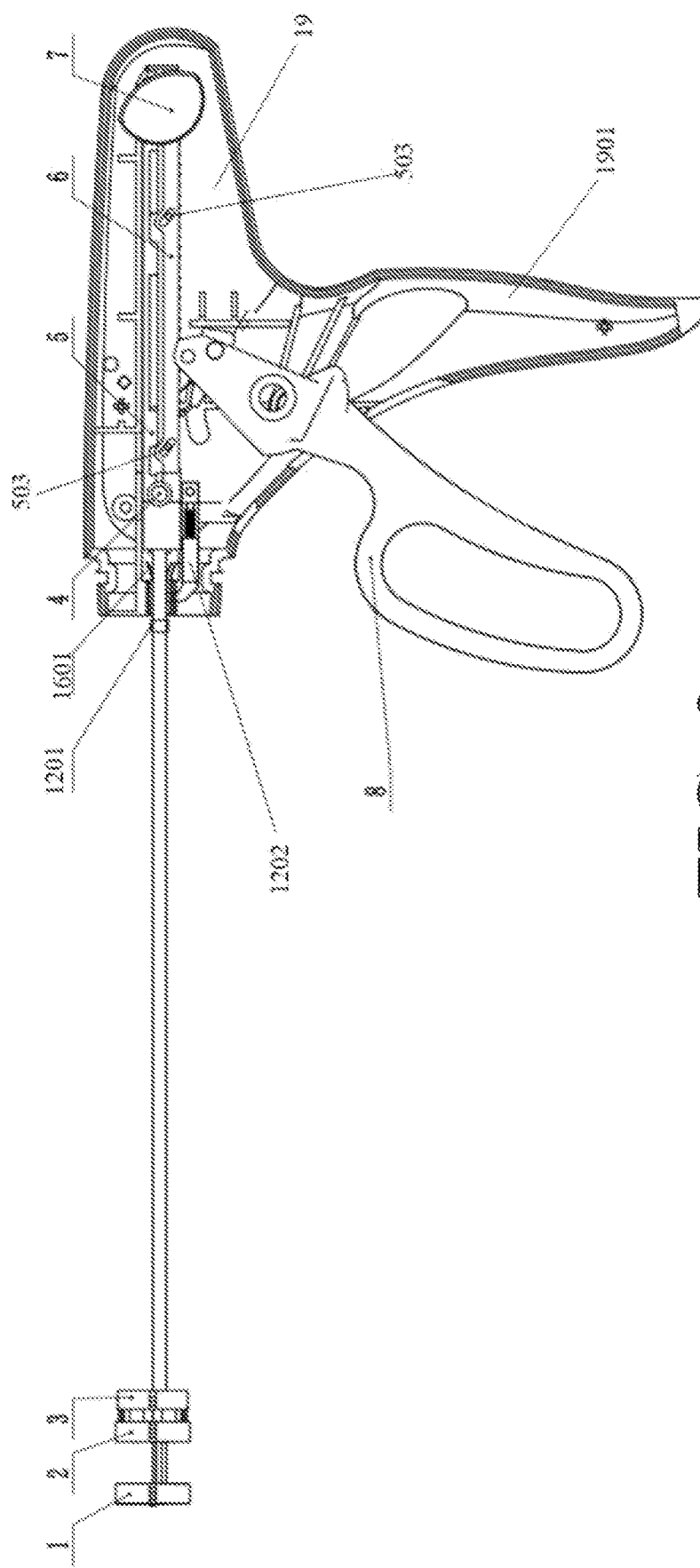
FIG. 9 is a cross-sectional view of the present disclosure.
Figure 11:
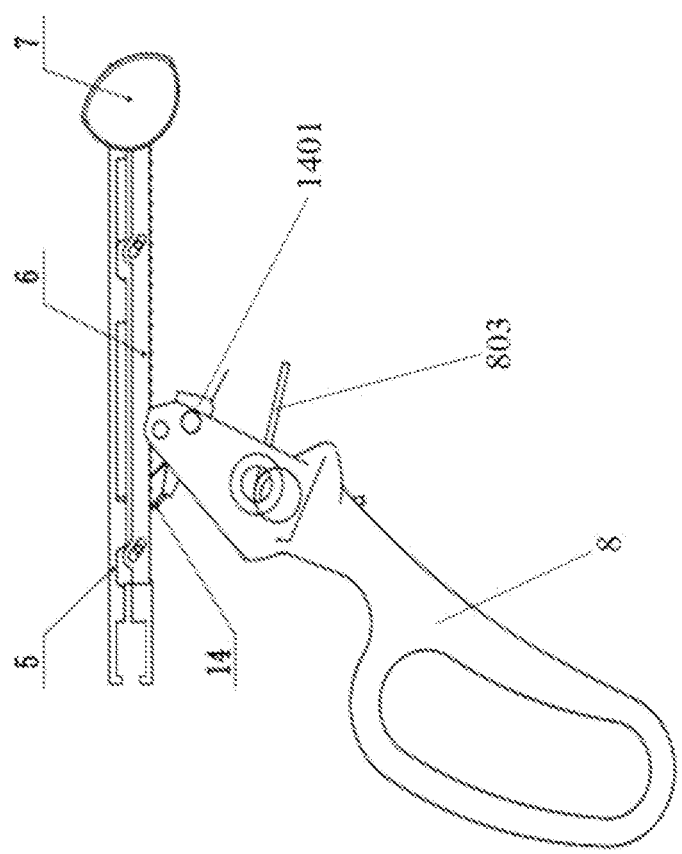
FIG. 11 is a partial schematic diagram of the operation assembly of the present disclosure.

As shown in FIGS. 7, 8, and 9, the stapler body mainly includes a shell 19, with a fixed handle 1901 at the lower part of the shell 19. The stapler body is made of relatively lightweight materials such as plastic. The stapler shell 19 has two halves that are fixed together by rivets and screws. The inside of the shell is uneven for fixing and installing various assemblies. The fixed handle 1901 is oblique backwards and downwards for a surgical operator to grip. Based on the overall weight evaluation of the stapler, a counterweight may be added appropriately.

As shown in FIGS. 7, 8, 9, 11, 12, 14 and 15, the trigger assembly is arranged in front of the fixed handle 1901. The trigger assembly includes an active handle 8 in front of the fixed handle, and the active handle 8 is installed on the fixed handle 1901 of the stapler through a fixing nut 802 and a corresponding bolt. When the fixed handle 1901 is held and the active handle 8 is pulled, the active handle can rotate around the installation point. A reset spring 803 is arranged on the bolt. After the active handle is pulled and then released, under the action of the reset spring, the active handle 8 can be reset and rebound. The reset spring 803 can generally be a torsion spring. A U-shaped groove is arranged at the top of the active handle, and a pawl 14 is installed in the groove. The rear end of the pawl 14 is rotatably installed in the groove of the active handle 8, and the pawl 14 is installed through a bolt and a nut. A reset spring (e.g., a torsion spring) is correspondingly arranged on the bolt, and the pre-tightening force of the reset spring causes the front end of the pawl 14 to rest against a spine at the bottom of a drive pin 5. When an external force is applied downwards on the pawl 14, the front end of the pawl 14 is separated from the spine. Once the external force disappears, under the action of the reset spring, the front end of the pawl rests against the spine again. The two sides of the pawl 14 extend outward to facilitate the downward external force applied by rams 6 to act on the pawl.

As shown in FIGS. 9, 11, 12, 14, 15 and 16, the opening and closing assembly mainly includes the drive pin 5, the rams 6, and reset buttons 7. The drive pin 5 is installed in the shell 19 and can be moved back and forth in the shell. The drive pin 5 has a long cylindrical structure and is provided with the spine 501 at the bottom. Two ram limiting columns 503 are arranged on each of two sides of the drive pin 5, and the 2 ram limiting columns 503 on each side are at two ends of the side of the drive pin 5. The ram limiting columns are integrated with the drive pin, and may also be designed as independent components to be installed on the drive pin. A traction spring installation cavity 507 is arranged at the top of the drive pin 5, and a traction spring installation column 506 is arranged at the front end of the traction spring installation cavity 507. A double fork arm structure is arranged at the front end of the drive pin 5, and includes an upper extension 502 and a lower extension 504 face to face in the front, and an accommodation cavity 508 in the middle. A reset button installation hole 505 is formed at the rear end of the drive pin 5. Kidney-shaped holes 601 are formed at two ends of the rams 6 respectively, and the kidney-shaped holes 601 are inclined high in the front and low at the back. A ram installation hole 602 is formed at the rear end of the ram 6. One ram 6 is installed on each of two sides of the drive pin 5. Reset button moving slots 1902 are formed on both sides of the shell 19, and a reset button shaft 702 passes through the left reset button moving slot, the left ram installation hole, the reset button installation hole 505, the right ram installation hole, and the right reset button moving slot in sequence. Two reset buttons 7 are installed at both ends of the reset button shaft 702. A traction spring 701 is placed in the traction spring installation cavity 507, with one end installed on the traction spring installation column 506 and the other end installed at the front end of an installation plate 510. The installation plate 510 is also in the traction spring installation cavity. A hole is formed at the rear end of the installation plate 510, and the middle part of the reset button shaft 702 penetrates through the hole, thereby achieving connection between the installation plate 510 and the reset button shaft 702. The 2 ram limiting columns 503 on both sides of the drive pin 5 penetrate through the 2 kidney-shaped holes 601 of the rams 6 respectively.

The following is a detailed description of the coordination between the trigger assembly and the opening and closing assembly to achieve forward and backward movement of the drive pin 5. In the initial state shown in FIG. 9, the reset buttons 7 are at the rear ends of the reset button moving slots 1902. At this time, under the action of the traction spring 701, the rams 6 are pulled onto the drive pin 5, that is, the bottom ends of the kidney-shaped holes 601 of the rams 6 are in contact with the ram limiting columns 503, the spine 501 is exposed, and the front end of the pawl 14 rests against the teeth of the spine 501. When the handle is held and the active handle 8 is pulled, the pawl 14 pushes the drive pin 5 forward through the spine 501. When the active handle 8 is released and the reset buttons 7 are pulled backwards, the reset buttons 7 first overcome the pulling force of the traction spring 701 to pull down the rams 6, that is, to make the top ends of the kidney-shaped holes 601 of the rams 6 come into contact with the ram limiting columns 503. The rams 6 move downward for a certain distance relative to the drive pin 5. On the one hand, the rams 6 cover the spine 501, and on the other hand, the rams apply an external force downwards to the pawl 14, causing the pawl 14 to rotate counterclockwise so that the pawl 14 detaches from the spine 501. At this point, the reset button shaft 702 is in contact with the rear wall of the reset button installation hole 505, and the reset buttons can be pulled backward to drive the drive pin 5 to move backward. In this process, the rams 6 cover the spine 501 all the time, and the rams 6 are reset under the action of the traction spring until the reset buttons are released. After the external force on the pawl 14 disappears, the pawl 14 is reset and rests against the spine again.

The main function of the trigger assembly in this example is to apply a force to drive the drive pin 5 to move forward, while the backward movement of the drive pin 5 is achieved by pulling the reset buttons 7 backward. It can be reasonably foreseen that the present disclosure drives an ejector plate pin and a cartridge pin to move forward and backward through the drive pin 5. Any driving assembly that can achieve forward and backward movement of the drive pin can be applied to the present disclosure, for example, the trigger assembly can be replaced with an electric motor to achieve the forward and backward movement of the drive pin. In this example, through the coordination of the pawl 14 and the spine, not only the operation of the surgical operator is facilitated, but also the structure is relatively stable and simple.

As shown in FIGS. 7, 8, 9, 10, 12, 13, 14 and 15, the extension assembly includes an anvil pin 17, a cartridge pin 16, an ejector plate pin 15, and an unlocking pin 12, the rear ends of which are all arranged in the stapler shell 19, and the ejector plate pin 15, the cartridge pin 16, and the anvil pin 17 are arranged successively along the direction from the left to the right of the stapler. The anvil pin 17, the cartridge pin 16, and the ejector plate pin 15 are all long strips, and each is made of materials with strong rigidity (e.g., metal). The rear end of the anvil pin 17 is installed at the front end of the stapler body and cannot be moved. The front ends of the ejector plate pin 15, the cartridge pin 16, and the anvil pin 17 are respectively connected to an ejector plate ring 3, a cartridge ring 2, and an anvil ring 1.

As shown in FIGS. 12, 13, 14 and 15, the rear end of the ejector plate pin 15 is connected to the front end of the drive pin 5, and the drive pin 5 drives the ejector plate pin 15 forward or backward together. The cartridge pin 16 is also driven forward or backward by the drive pin 5. However, unlike the ejector plate pin 15, when the cartridge pin 16 drives the cartridge ring 2 and the anvil ring 1 to rest in place, the active handle 8 is pulled, and the drive pin 5 continues to drive the ejector plate pin 15 forward. However, the drive pin 5 is to be detached from the cartridge pin 16, so that even if the drive pin 5 continues to move forward, the cartridge pin 16 cannot be driven forward by the drive pin. The present disclosure is implemented through a limiting button 4. Specifically, a cartridge pin rear end protrusion 1602 at the tail end of the cartridge pin 16 is convex, and the cartridge pin rear end protrusion 1602 is placed in the accommodation cavity 508 at the front end of the drive pin 5. The body of the cartridge pin 16 passes through the gap between the upper extension 502 and the lower extension 504 of the drive pin 5. A limiting button end convex block 403 is arranged at the inner end of the limiting button 4. A limiting button moving slot 1903 is arranged at the left side of the shell 19, and the limiting button moving slot 1903 is a straight slot parallel to the reset button moving slot 1902. The outer end of the limiting button 4 extends out of the shell from the limiting button moving slot 1903, and a limiting button operating part 402 at the outer end is used by the surgical operator to hold and operate the limiting button 4. The limiting button end convex block 403 of the limiting button 4 is in the accommodation cavity 508. When the limiting button end convex block 403 is at the rear end of the cartridge pin 16 and in contact with the rear end of the cartridge pin, the limiting button end convex block 403 and the cartridge pin rear end protrusion 1602 together fill the accommodation cavity 508, and the drive pin 5 pushes the cartridge pin 16 to move forward together through the limiting button end convex block 403. When the cartridge ring 2 rests against the anvil ring 1, the limiting button 4 is pulled outward or the limiting button 4 is pushed inward to separate the limiting button end convex block 403 from the cartridge pin rear end protrusion 1602. At this point, the drive pin 5 cannot continue to push the cartridge pin 16. Specifically, there is a distance between the rear wall of the accommodation cavity 508 of the drive pin and the cartridge pin rear end protrusion 1602. In the process of the drive pin 5 continuing to move forward, the rear wall of the accommodation cavity 508 cannot come into contact with the cartridge pin rear end protrusion 1602, so that the drive pin 5 cannot push the cartridge pin to move forward. Nevertheless, the distance is enough for the ejector plate pin to continue moving forward, allowing the ejector plate ring 3 to push out an anastomotic nail in the cartridge ring to anastomose broken ends of tissue together. When the cartridge pin is to be driven to move backwards, the drive pin 5 is pulled backwards, and the upper extension and lower extension of the drive pin 5 are in contact with the front wall of the cartridge pin rear end protrusion 1602 to drive the cartridge pin to move backwards.

In order to enable the surgical operator to visually see the travel distance and position of the cartridge pin and the ejector plate pin in a surgical process, the present disclosure may also indicate the travel distance through the coordination between the limiting button 4 and the limiting button moving slot 1903, and graduations are provided on the limiting button moving slot 1903. In the present disclosure, the left side of the accommodation cavity 508 is enclosed and an avoidance hole is formed on the left wall. The limiting button 4 passes through the avoidance hole and enters the accommodation cavity. In this design, when the drive pin 5 moves, the limiting button can move with the drive pin.

Figure 13:
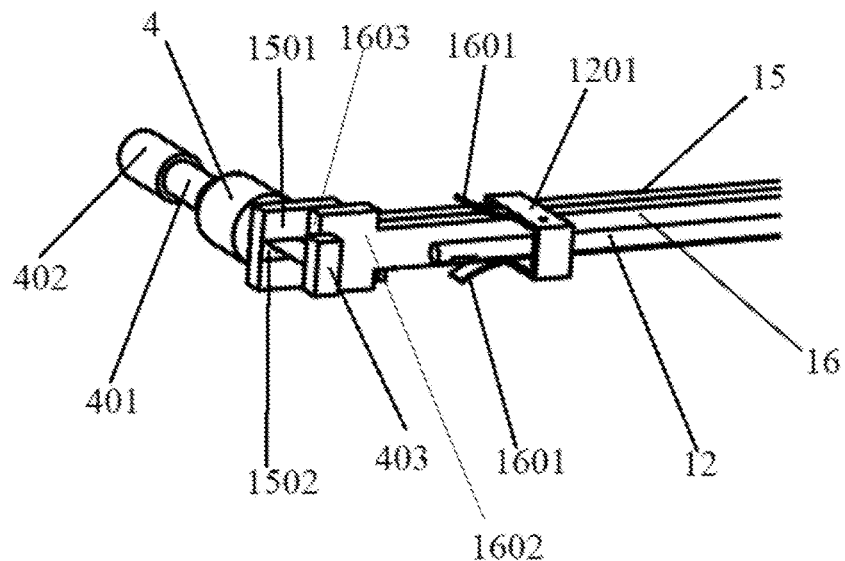
FIG. 13 is a schematic diagram of coordination between the limiting button, the cartridge pin, the ejector plate pin and the unlocking pin.

The present disclosure further designs another solution to achieve synchronous movement of the limiting button 4. An avoidance hole 1502 is formed at the rear end of the ejector plate pin 15, and the limiting button 4 passes through the avoidance hole. When the drive pin drives the ejector plate pin 15 to move, the limiting button 4 may move together with the ejector plate pin 15. The surgical operator can visually know how far the ejector plate pin 15 has moved by the movement distance of the limiting button 4, and then know how far the ejector plate ring 3 moves. Referring to FIG. 13, an ejector plate pin rear end protrusion 1501 is arranged at the tail end of the ejector plate pin 15, and the protrusion has a larger area and is more convenient for forming the avoidance hole 1502 on the ejector plate pin rear end protrusion 1501. At the same time, the ejector plate pin 15 and the drive pin 5 shown in FIG. 13 are detachably connected, that is, the ejector plate pin rear end protrusion 1501 is placed in the accommodation cavity 508, and the ejector plate pin rear end protrusion 1501 has a convex structure. The body of the ejector plate pin 15 passes through the gap between the upper extension 502 and the lower extension 504 of the drive pin 5. The rear wall of the ejector plate pin rear end protrusion 1501 is in contact with the rear wall of the accommodation cavity 508, and the drive pin can directly push the ejector plate pin forward. The ejector plate pin is pulled backward through the coordination between the upper extension, the lower extension, and the ejector plate pin rear end protrusion.

Figure 10:
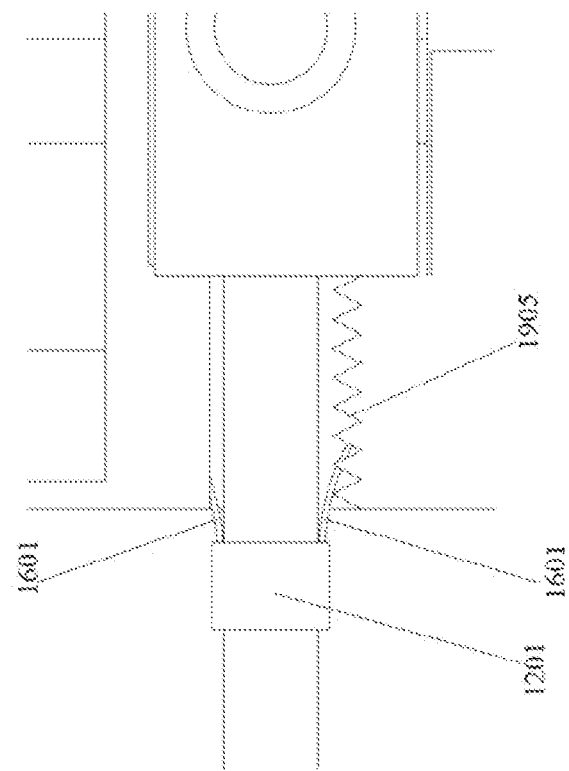
FIG. 10 is a partially enlarged view of the present disclosure (the cartridge pin elastic wings and the clamping groove of the shell).
Figure 12:
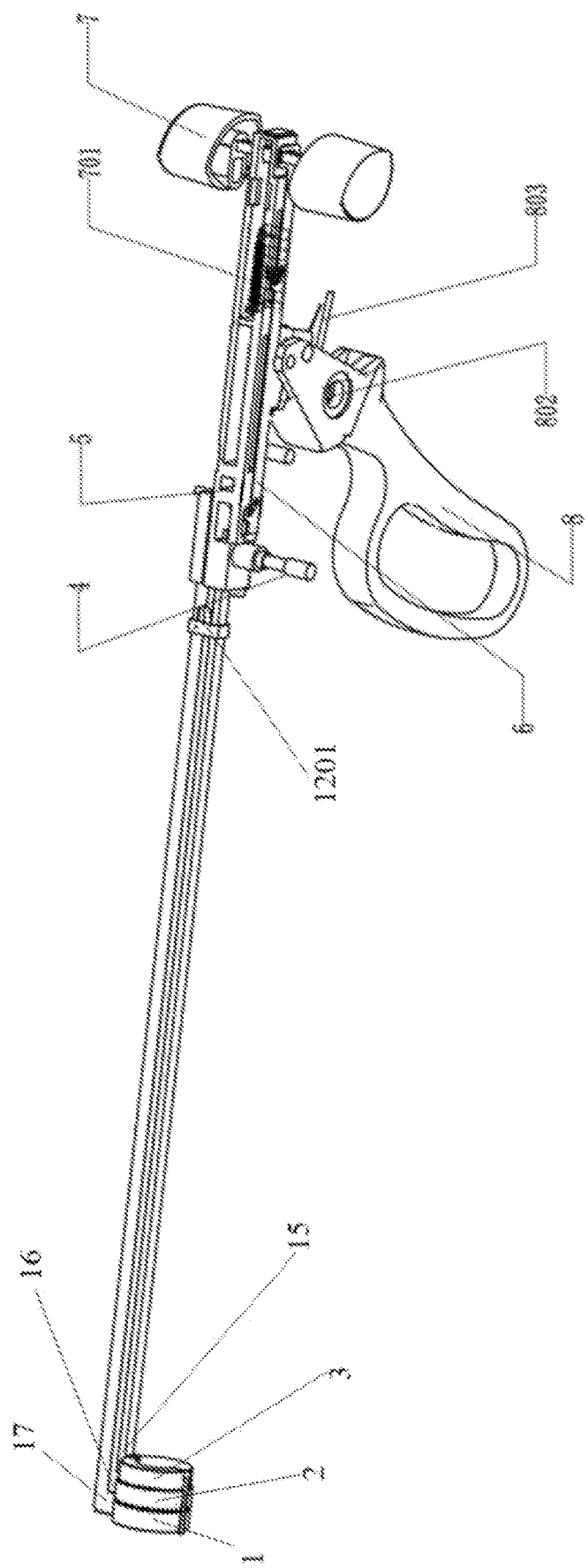
FIG. 12 is a schematic diagram of coordination between the limiting button, the active handle and the drive pin.
Figure 14:
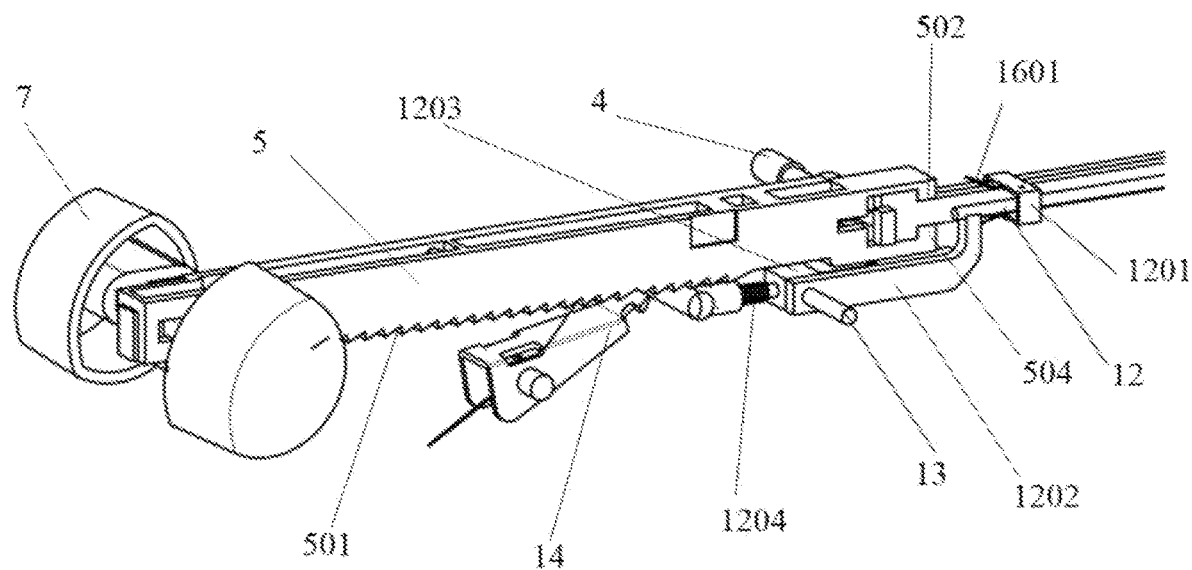
FIG. 14 is a schematic diagram of coordination between the drive pin, the limiting button, the cartridge pin, the ejector plate pin and the unlocking pin.
Figure 15:
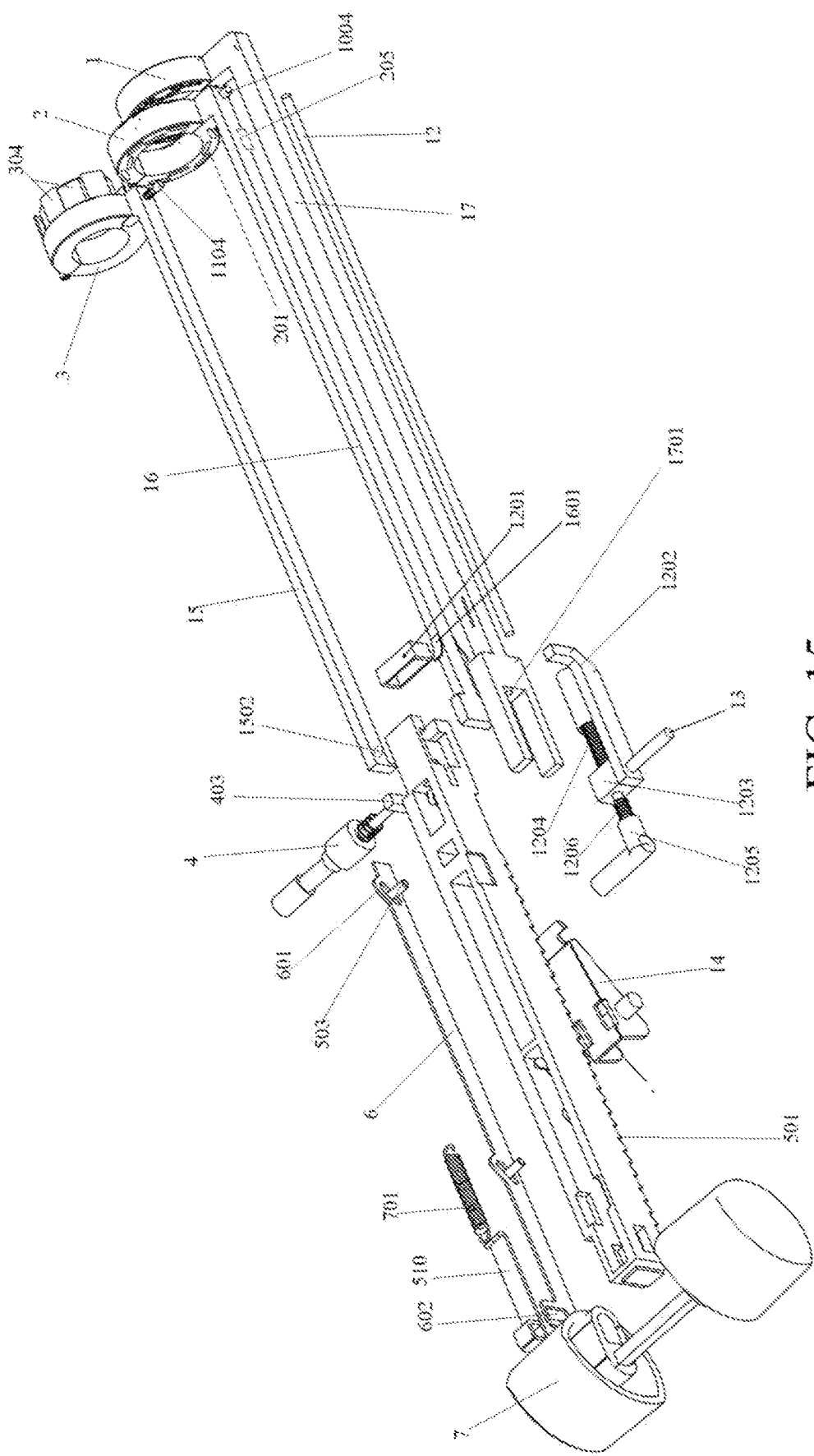
FIG. 15 is an exploded view of the coordination relationship between the drive pin, the limiting button, the cartridge pin, the ejector plate pin and the unlocking pin.
Figure 16:
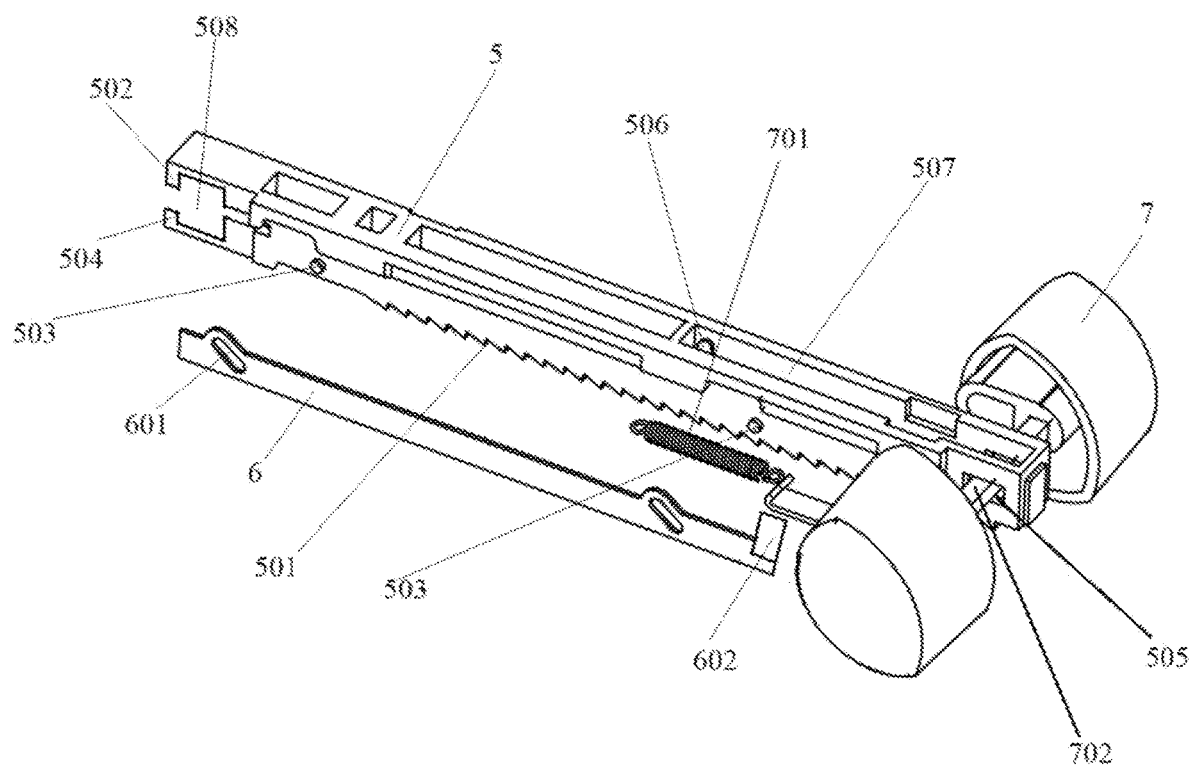
FIG. 16 is an exploded view of the drive pin, the reset button and the ram.

The arrangement and function of the unlocking pin 12 are described below in conjunction with FIGS. 9, 10, 12-15, 17 and 19. Cartridge pin elastic wings 1601 are arranged on the cartridge pin 16. As shown in FIG. 10, one cartridge pin elastic wing 1601 is arranged on each of the upper and lower surfaces of the cartridge pin. Correspondingly, at the front end of the shell 19, two rows of clamping grooves 1905 are arranged up and down on the inner wall of the shell 19 (the upper row of clamping grooves is not shown in FIG. 10). An unlocking press plate 1201 is also arranged on the cartridge pin 16 and connected to the unlocking pin 12. Referring to FIGS. 13-15 and 17, a long hole is formed along the length direction inside in the anvil pin 17, and an unlocking press pin is in the long hole. The rear end of the unlocking pin passes through an unlocking pin through hole 1701 and is connected to the unlocking press plate 1201. As shown in FIG. 8, an unlocking button moving slot 1904 is arranged on the right side of the shell 19. The unlocking button 13 passes through the unlocking button moving slot 1904, and then is connected to the rear end of the unlocking pin 12 in the shell. The unlocking button 13 is held by hand to push the unlocking pin forward or backward towards the anvil ring. As shown in FIGS. 14 and 15, for the convenience of operation, the unlocking button 13 is arranged at the rear end of an L-shaped connecting pin 1202 in the present disclosure. The front end of the connecting pin 1202 is tilted upwards and connected to the unlocking pin 12. A sliding seat 1203 is arranged at the rear end of the connecting pin 1202, and a guide column 1205 is sheathed with the sliding seat 1203 which can move back and forth along the guide column. The guide column 1205 is installed in the shell, and the operation is more stable through the guidance of the guide column. The sliding seat, the unlocking button, and the connecting pin may be integrated, or assembled together in split structures.

Based on FIGS. 9 and 10, the opening direction of the cartridge pin elastic wings 1601 is towards the rear end. When the drive pin 5 drives the cartridge pin to move forward, after the cartridge pin elastic wings 1601 reach the clamping groove area, a surgical operator can hear a "click" sound, allowing the surgical operator to know through the sound where the cartridge ring has reaches until the cartridge ring rests against the anvil ring. The cartridge pin elastic wings are clamped in the clamping groove to achieve positioning of the cartridge pin, and even if the drive pin moves backward, it is difficult to drive the cartridge pin to move backward. When the unlocking button 13 is held to drive the unlocking pin 12 backward, the unlocking press plate gradually moves backward and presses the cartridge pin elastic wings 1601 to retract. The cartridge pin elastic wings 1601 are separated from the clamping groove 1905, so that the drive pin 5 can move backward together with the cartridge pin. When the cartridge pin is to move forward again, the unlocking pin 12 is pushed forward, and the unlocking press plate 1201 is gradually separated from the cartridge pin elastic wings 1601. The cartridge pin elastic wings 1601 lose the pressure of the unlocking press plate 1201 and bounce open, and after the cartridge pin is pushed forward to the position, the cartridge pin elastic wings are clamped in the clamping groove 1905.

As shown in FIG. 15, both ends of the sliding seat 1203 and the guide column 1205 are sheathed with a second unlocking pin spring 1206 and a first unlocking pin spring 1204 respectively. After the unlocking button is released, the unlocking pin springs (1204, 1206) may drive the unlocking pin 12 back to the initial position (i.e., the unlocking press plate 1201 is in front of the cartridge pin elastic wings 1601 without compressing the cartridge pin elastic wings), to avoid misoperation. In this case, the operation changes. When the drive pin drives a cartridge to move forward, the cartridge pin elastic wings are open, and the surgical operator can hear a "click" sound, and after the designated position is reached, the cartridge pin elastic wings are clamped in the clamping groove. The difference is that when the cartridge pin is to move backward, the unlocking press plate 1201 is pulled through the unlocking button 13 to compress the cartridge pin elastic wings 1601 (maintained in the compressed state), the drive pin 5 drives the cartridge pin to move backward to the designated position, and then the unlocking button 13 is released. Under the action of the second unlocking pin spring 1206, the unlocking press plate 1201 is reset, and the cartridge pin elastic wings are opened. At this point, the cartridge pin may be directly driven forward without pulling the unlocking button 13 to make the unlocking press plate 1203 release the cartridge pin elastic wings.

The unlocking press plate in FIG. 15 is in a frame shape or can be made in a "[" shape or the like, as long as the unlocking press plate can compress the cartridge pin elastic wings to retract. The unlocking press plate may be designed in an independent structure, installed on the unlocking press pin, or integrated with the unlocking pin.

The cartridge pin, the ejector plate pin, and the anvil pin are elongated. The unlocking pin as a whole is also elongated. The rear end of the unlocking pin is curved.

Figure 17:
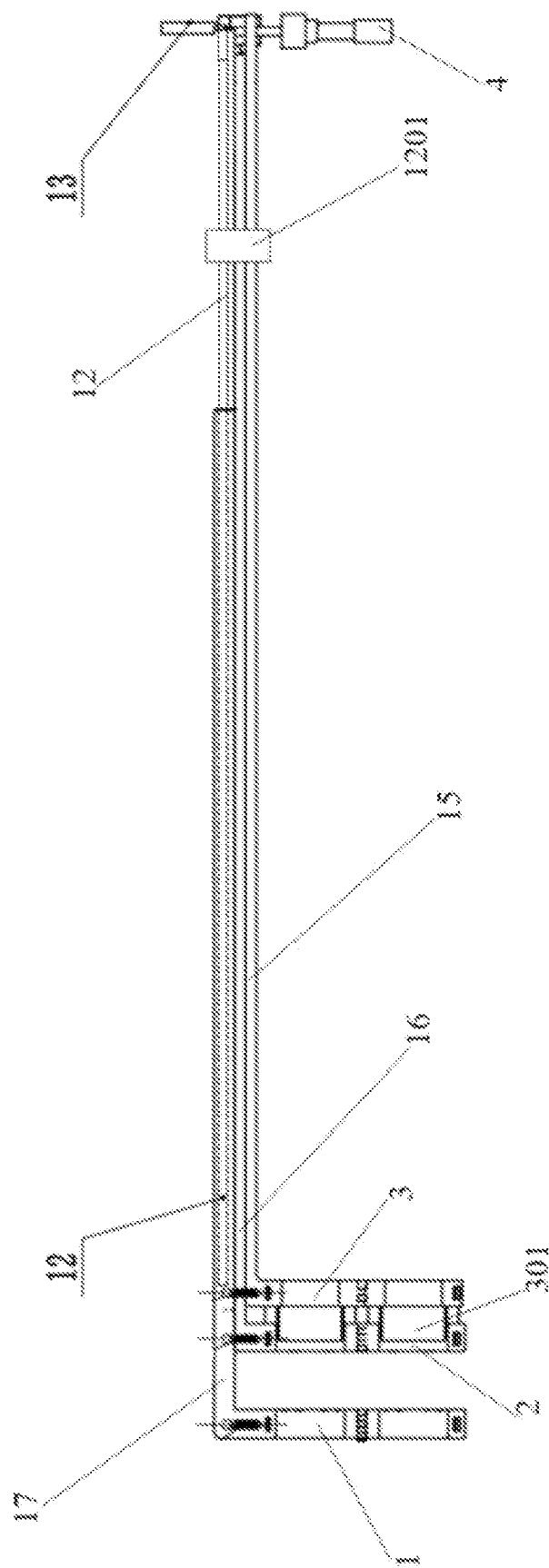
FIG. 17 is a schematic diagram I of the extension assembly.
Figure 18:
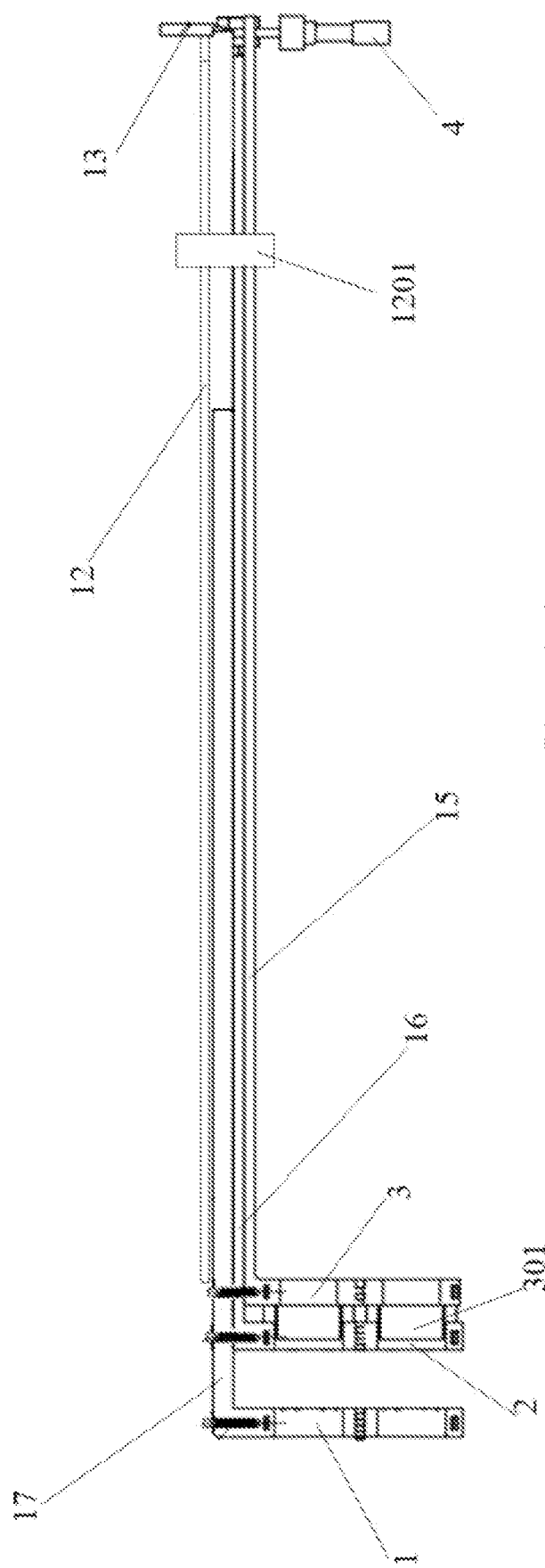
FIG. 18 is a schematic diagram II of the extension assembly.

Referring to FIGS. 17 and 18, the unlocking pin shown in FIG. 17 is inserted into the long hole of the anvil pin 17, and the long hole has a guidance function. The unlocking pin in FIG. 18 is arranged outside the anvil pin, and can also achieve the function of the unlocking pin. To ensure stable movement, a guide ring (not shown in the figure) may be arranged outside the anvil pin and the unlocking pin passes through the guide ring. In addition, preferably, a complete guide ring is arranged along the length direction of the unlocking pin, so that the guide ring not only has a guidance, but also has a similar function to the anvil pin, that is, when the unlocking pin moves in a limited space, the forward force applied to the unlocking pin is more easily converted into a force perpendicular to the direction of the pin body, thereby more effectively pushing the unlocking column.

As shown in FIGS. 20-24, the execution assembly includes the anvil ring 1, the cartridge ring 2, the ejector plate ring 3 and a circular blade 301, and anastomotic nails are installed on the cartridge ring 2.

Figure 21:
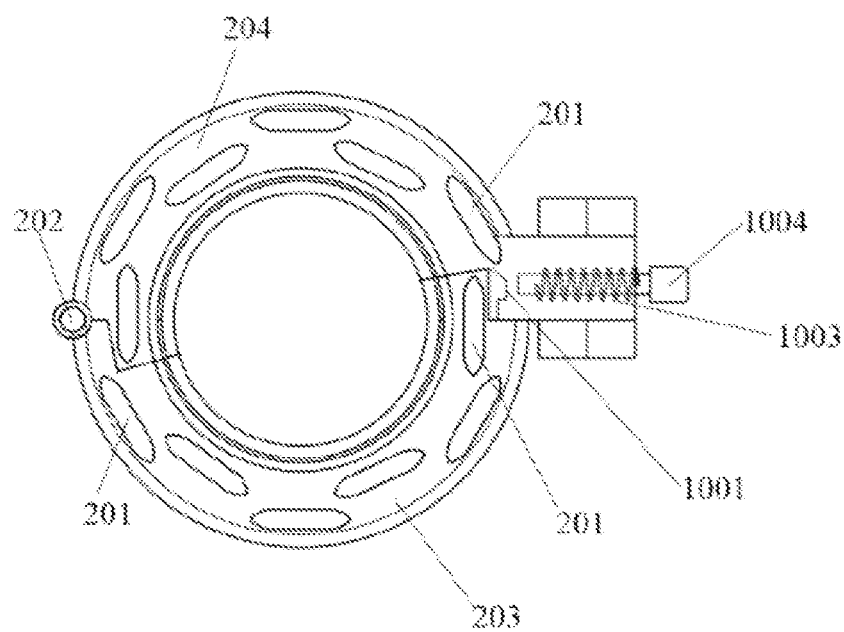
FIG. 21 is a schematic diagram of the cartridge ring and the lock catch.
Figure 22:
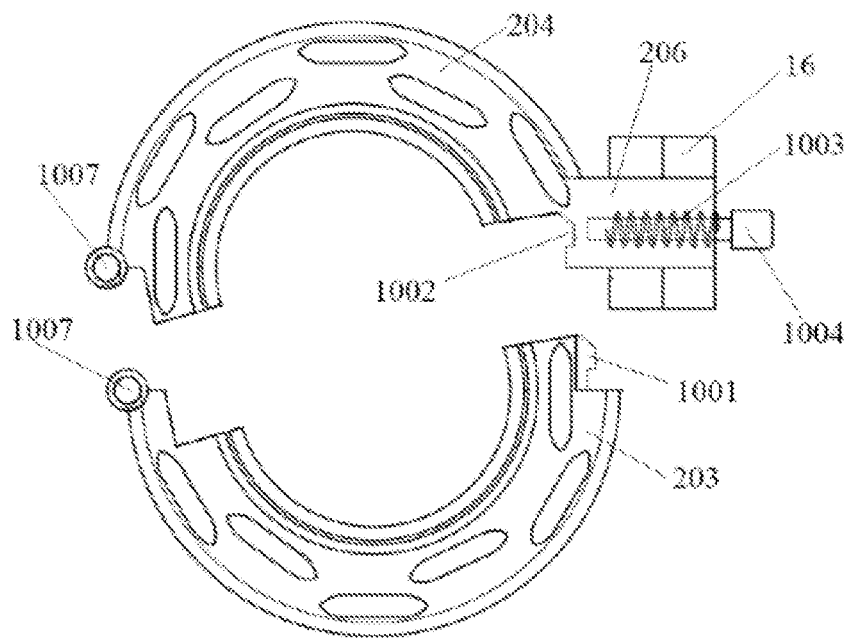
FIG. 22 is an exploded view of the cartridge pin.

The anvil ring 1, the cartridge ring 2, and the ejector plate ring 3 are all in a circular shape, and are all designed as a structure of two half ring structures forming a circular ring in the present disclosure. Mainly referring to the cartridge ring shown in FIGS. 20, 21 and 22, the splicing method of the two half rings and how to achieve the closure and opening of the circular ring are described. The cartridge ring 2 includes a first half ring 203 and a second half ring 204. The cartridge ring 2 is integrally on one side of the front end of the cartridge pin. One end of the second half ring 204 is connected to the front end of the cartridge pin 16, and the other end of the second half ring 204 is connected to one end of the first half ring 203. The first half ring 203 can rotate relative to the connection point. A connection hinge 202 is shown in FIG. 21. The first half ring and the second half ring are connected through the connection hinge 202. It can be foreseen that the connection hinge 202 may also be replaced with a rotating shaft. As shown in FIG. 22, rotating shaft holes 1007 are formed at the connecting ends of both the half rings, and a rotating shaft can be installed in the rotating shaft holes to achieve rotation. A cartridge pin lock catch 10 is arranged in the present disclosure. Specifically, at one end where the second half ring 204 is connected to the cartridge pin, a female buckle 1002 is arranged on the second half ring 204, and a male buckle 1001 is arranged at the corresponding end of the first half ring 203. The male buckle 1001 can be buckled into the female buckle 1002 to achieve assembly of the first half ring and the second half ring into a cartridge ring. The male buckle 1001 can be pushed out of the female buckle to unlock the two half rings. Through holes are formed at one end of the second half ring 204 and the cartridge pin, and an unlocking column 1004 is inserted into the through holes. The unlocking column is perpendicular to the length direction of the cartridge pin, and the unlocking column 1004 is pushed towards the direction of the male buckle 1001 to push the male buckle away from the female buckle by the unlocking column. The unlocking column 1004 is sheathed with an unlocking spring 1003. After the external force applied to the unlocking column disappears, the unlocking column resets under the action of the unlocking spring 1003. The male buckle 1001 is an elastic arm made of an elastic material preferably. From FIGS. 21 and 22, it can be seen that two layers of anastomotic nails 201 are arranged on the cartridge ring. The ends of both the half rings are L-shaped. At the splicing section, one of the half rings is thicker and the other is thinner. This allows for the installation of anastomotic nails in the thicker section, allows for the arrangement of the anastomotic nails in the splicing section, and avoids the problem of anastomotic missing during anastomosis. The height and length of the anastomotic nails may be different, and may be nonabsorbable metal nails or absorbable nails, which can be configured as needed.

The end of the second half ring 204 may be integrally formed with the cartridge pin 16, or may have a split installation structure. As shown in FIG. 22, a ring installation seat 206 is arranged at the end of the second half ring 204. The ring installation seat 206 is inserted into a through hole on the cartridge pin 16, and then tightened with a screw. The unlocking column is inserted into a through hole of the ring installation seat 206. Due to high disinfection requirements of surgery, staplers are disposable consumable appliances with high cost. The present disclosure designs a split installation structure, so that a cartridge ring, an ejector plate ring and an anvil ring can be separated from the stapler body (including a cartridge pin, an ejector plate pin and an anvil pin). The cartridge ring, the ejector plate ring and the anvil ring are used as disposable consumable appliances, while the other components can be disinfected and reused, thereby greatly saving costs and reducing surgical expenses.

Figure 23:
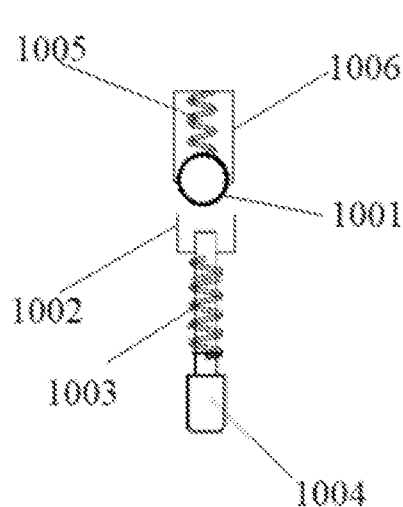
FIG. 23 is an example of the male buckle and the female buckle.

FIG. 23 shows another structure of a male buckle and a female buckle. A male buckle groove 1006 is formed at one end of a first half ring 203, and the male buckle 1001 is a sphere and is installed in the male buckle groove 1006 through an expansion spring 1005. A part of the sphere is exposed outside the male buckle groove, and the exposed part of the sphere is buckled into the female buckle 1002 to achieve splicing and locking. An unlocking column 1004 is used for pushing the sphere out of the female buckle to achieve separation.

Figure 24:
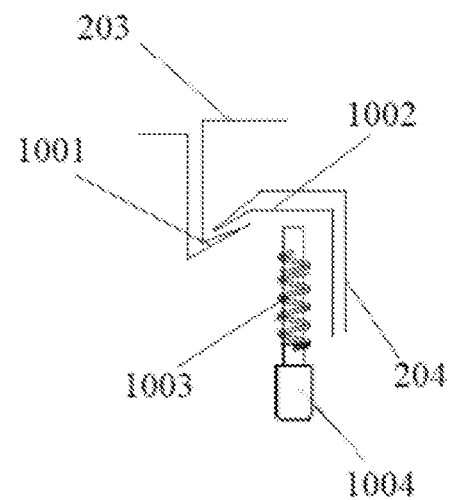
FIG. 24 is another example of the male buckle and the female buckle.

FIG. 24 shows another structure of a male buckle and a female buckle. A hook-shaped male buckle 1001 is arranged on a first half ring 203, and a hook-shaped female buckle 1002 is arranged on a second half ring 204. The two hook-shaped structures are used for achieving locking, and an unlocking column is used for pushing the female buckle 1002 outward to achieve separation. The female buckle 1002 is made of an elastic material preferably.

The above schematically illustrates three structural forms of the male and female buckles, and other applicable structural forms that can achieve locking of two half rings and can be unlocked with the help of unlocking columns can be applied to the present disclosure. For example, the expansion spring and the sphere shown in FIG. 23 may be replaced with a pin, the pin is inserted into the female buckle to achieve locking, and the pin is pushed out of the female buckle by an unlocking column to release the locking.

Figure 27:
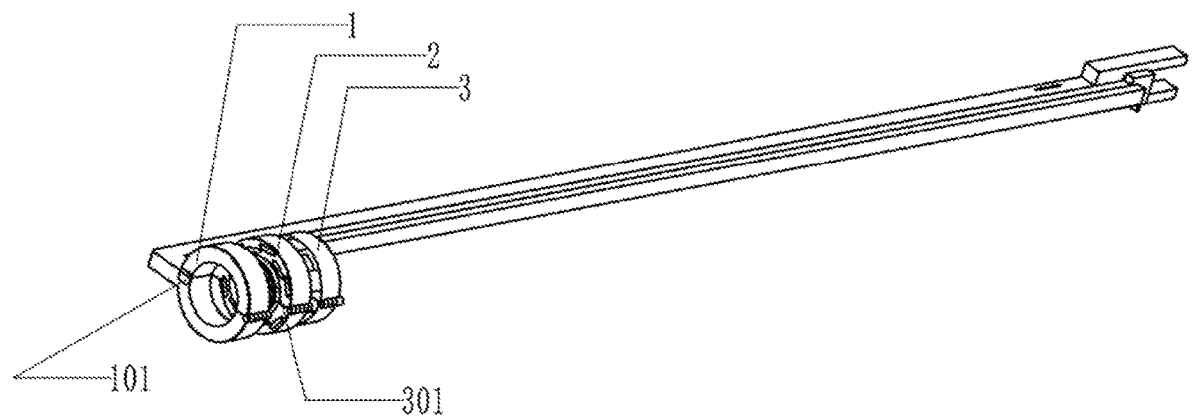
FIG. 27 is a schematic diagram II of the anvil ring, the cartridge ring and the ejector plate ring when closed.

The anvil ring and the ejector plate ring are also formed by two half rings, and have basically the same structures as the cartridge ring except for the absence of anastomotic nails. The anvil ring and the ejector plate ring are provided with an anvil pin lock catch 9 (including a male buckle 901 and a female buckle 902) and an ejector plate pin lock catch 11 (including a male buckle 1101 and a female buckle 1102) respectively. One end of one half ring of the anvil ring and one end of one half ring of the ejector plate ring are connected to an anvil pin and an ejector plate pin, respectively. Referring to FIG. 27, the cartridge ring 2 is between the anvil ring 1 and the ejector plate ring 3, the ejector plate ring 3 is at the near-end (i.e., near a surgical operator), and the anvil ring 1 is at the far-end (i.e., far away from the surgical operator). An ejector plate 304 and an anvil (not shown in the figure) corresponding to the anastomotic nails on the cartridge ring 2 are arranged on the ejector plate ring 3 and the anvil ring 1, respectively. The ejector plate ring 3 is also provided with a circular blade 301 on the outer edge of the ejector plate 304. The coordination of the ejector plate, the anvil, and the anastomotic nails is a conventional technique and will not be described in detail.

Figure 20:
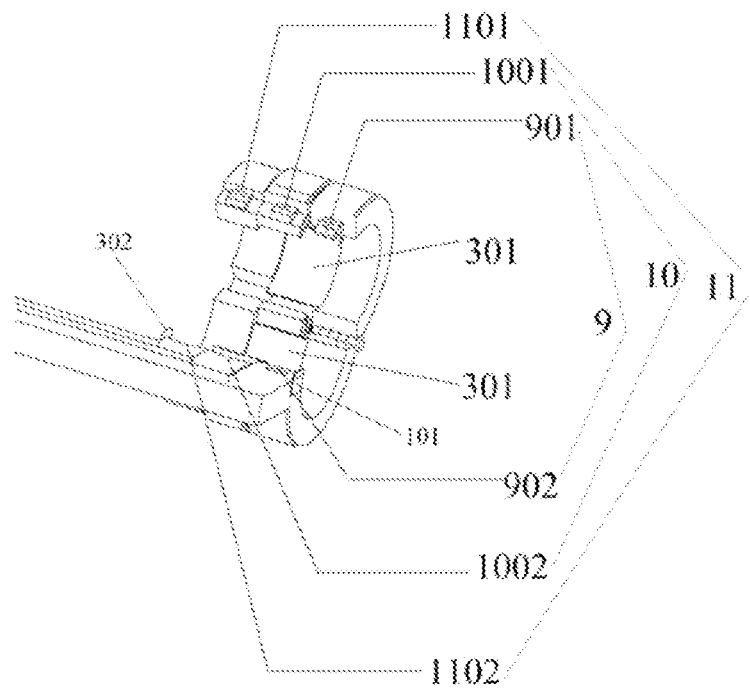
FIG. 20 is a schematic diagram of the anvil ring, the cartridge ring and the ejector plate ring when opened.
Figure 26:
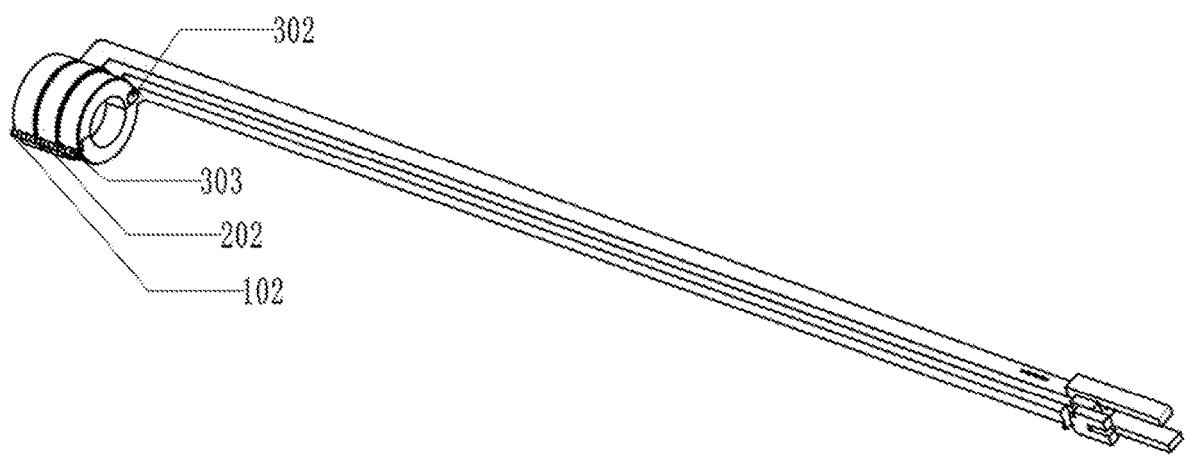
FIG. 26 is a schematic diagram I of the anvil ring, the cartridge ring and the ejector plate ring when closed.
Figure 28:
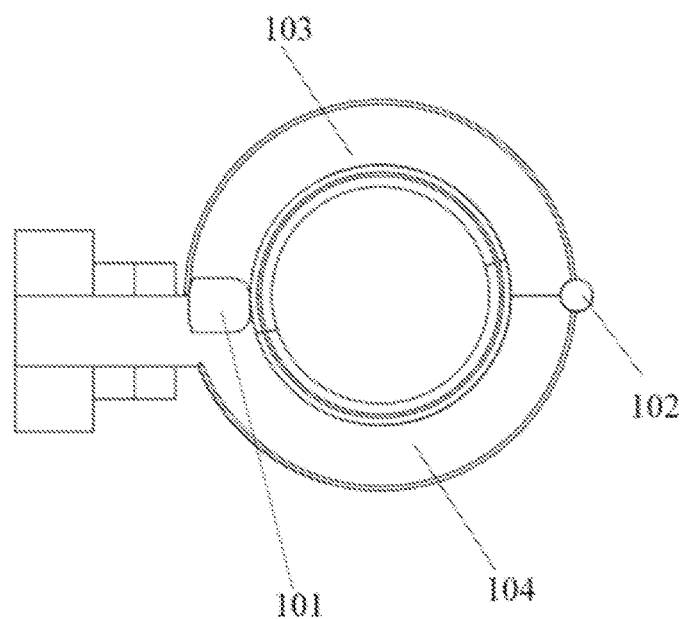
FIG. 28 is a schematic diagram of the ejector plate ring and the protecting plate.
Figure 29:
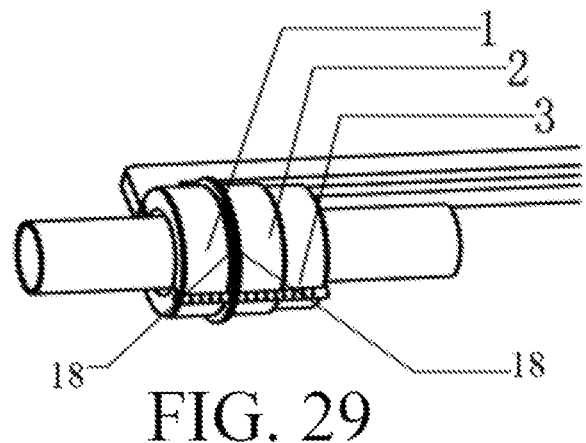
FIG. 29 is a partial schematic diagram of tissue eversion end-to-end anastomosis (taking intestinal tissue as an example).
Figure 30:
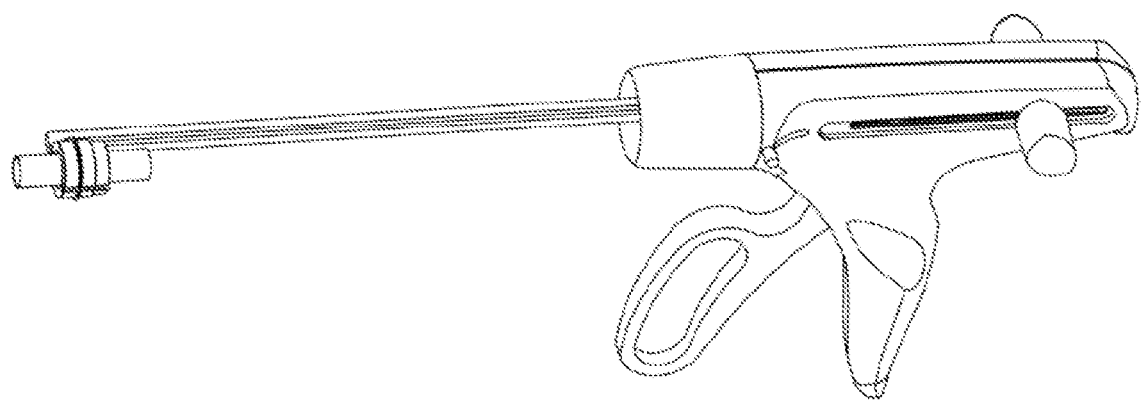
FIG. 30 is a complete schematic diagram of the example in FIG. 29.

Referring to FIGS. 20, 27 and 28, a second half ring 104 of an anvil ring 1 is connected to an anvil pin 17. An anvil protecting plate 101 is arranged at the end of the second half ring 104 or on the anvil pin 17. The anvil protecting plate 101 is on the outer side of the anvil ring (the side near the cartridge ring is the inner side). When a first half ring 103 and the second half ring 104 are spliced and locked, the splicing area is covered by the anvil protecting plate 101. Referring to FIGS. 20 and 26, at the connection between the ejector plate ring 3 and the ejector plate pin 15, an ejector ring protecting plate 302 is at the end of the ejector plate ring or on the ejector plate pin. The ejector ring protecting plate 302 is arranged on the outer side of the ejector plate ring (the side near the cartridge ring is the inner side). When the two half rings are spliced and locked, the splicing area is covered by the ejector ring protecting plate 302. Referring to FIGS. 26, 27 and 29, during anastomosis operation, broken ends of the intestine are everted, and the cartridge ring 2 rests against the anvil ring 1. Then, the ejector plate ring 3 is pushed, and the ejector plate pushes an anastomotic nail to anastomose the two broken ends of the intestine. At the same time, the excess everted tissue is excised by the circular blade. A tissue groove (not shown in the figure) is reserved where the anvil ring and the cartridge ring near the anvil pin and the cartridge pin, and the excised tissue falls into the tissue groove. During pushing the ejector plate ring, due to the presence of the ejector ring protecting plate, the force applied to the ejector plate pin 15 can be transmitted to the first half ring (i.e., the upper half ring in FIG. 20) through the ejector ring protecting plate, making the overall force on the ejector plate ring uniform to avoid insufficient thrust on the first half ring. Due to the anvil protecting plate 101, the splicing area of the anvil ring is covered from the outside to avoid detachment of the male buckles from the female buckles under external forces, ensuring the overall stability of the anvil ring under stress. The protecting plate may be made of metal or other hard materials.

Figure 19:
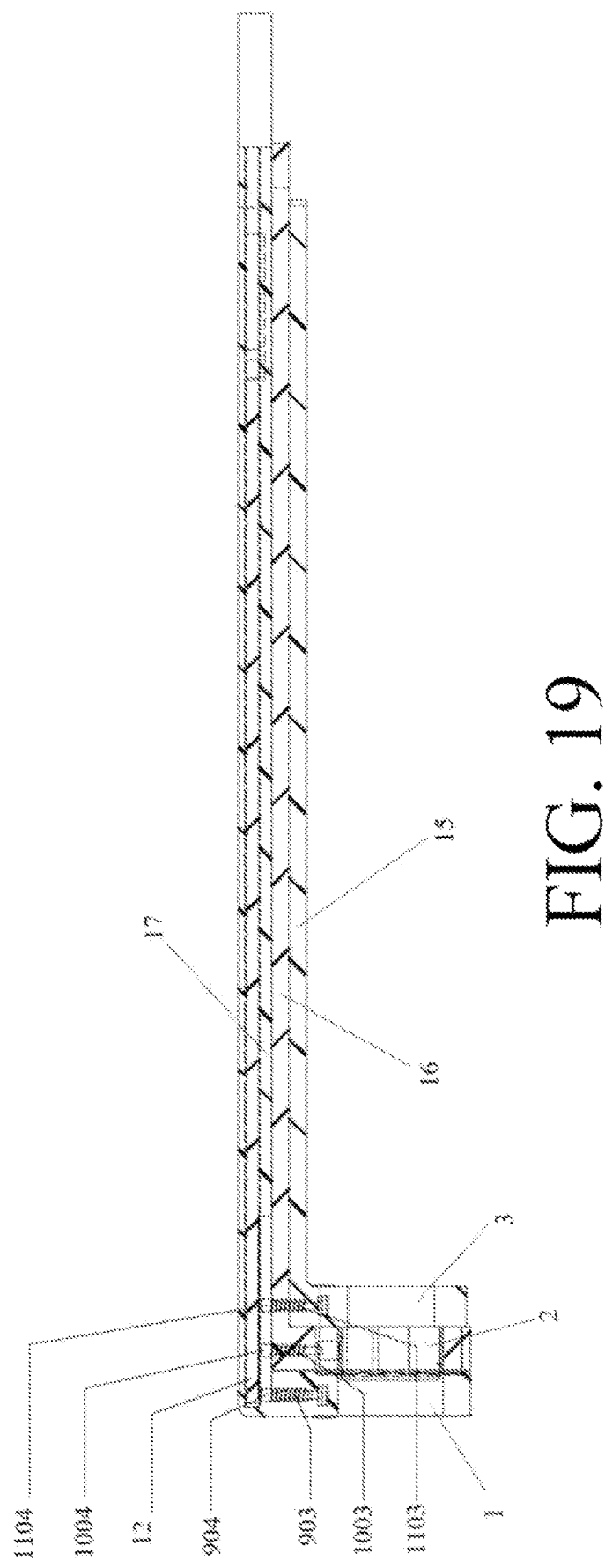
FIG. 19 is a schematic diagram of the unlocking buckle in front of the unlocking pin.

Referring to FIGS. 15, 17 and 19, the following illustrates how the present disclosure achieves unlocking of the lock catches through the unlocking pin 12. As the unlocking pin is in the anvil pin 17, the unlocking columns corresponding to the anvil ring, the cartridge ring, and the ejector plate ring pass through the corresponding pin bodies to enter the anvil pin. Specifically, the unlocking column on the anvil ring 1 enters the anvil pin through a hole on the anvil pin; the unlocking column on the cartridge ring 2 passes through the cartridge pin, and then enters the anvil pin through an avoidance slot on the anvil pin; and the unlocking column on the ejector plate ring 3 passes through the ejector plate pin 15, passes through an avoidance slot 205 on the cartridge pin 16, and then enters the anvil pin through an avoidance slot on the anvil pin. The unlocking pin shown in FIG. 17 is not pushed to the end of the anvil pin (the ring shown in the figure is open, but actually in a locking state shown in FIG. 26 during surgical operation). When the unlocking pin is pushed to the position shown in FIG. 19, the unlocking pin 12 pushes the unlocking columns of the ejector plate ring, the cartridge ring, and the anvil ring to move from the anvil pin to the ejector plate pin, and the unlocking columns will unlock the male buckles and the female buckles through the methods mentioned earlier. As shown in FIG. 18, the unlocking pin 12 is entirely outside the anvil pin. Correspondingly, the unlocking columns corresponding to the anvil ring, the cartridge ring, and the ejector plate ring must pass through the anvil pin to be pushed by the unlocking pin 12.

Due to relative displacement along the length direction of the pin bodies between the ejector plate pin and the cartridge pin, as well as between the ejector plate pin, the cartridge pin and the anvil pin, when the unlocking column of the ejector plate pin passes through the cartridge pin, enters or passes through the anvil pin, and the unlocking column of the cartridge pin enters or passes through the anvil pin, avoidance slots (e.g., the avoidance slot 205 as shown in FIG. 15) extending along the length direction of the pin bodies need to be arranged on the cartridge pin and the anvil pin to avoid obstructing the unlocking columns of the ejector plate ring and the cartridge ring.

Figure 25:
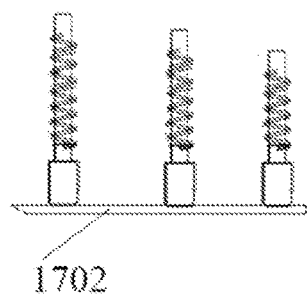
FIG. 25 is a schematic diagram of three unlocking columns when connected.

As shown in FIG. 25, from left to right are the unlocking columns corresponding to the ejector plate ring, the cartridge ring and the anvil ring. To facilitate the unlocking pin to push the end of each unlocking column, in the present disclosure, 3 unlocking columns are connected through a connecting plate 1702, and an inclined plane is formed at one end of the connecting plate 1702. The unlocking pin is inserted into the bottom of the connecting plate 1702 through the inclined plane, making it easy to push the unlocking columns.

The unlocking pin of the present disclosure is used on the one hand to open the lock catches on the cartridge ring, and the like, and on the other hand to drive the unlocking press plate to retract the cartridge pin elastic wings, thereby driving the cartridge pin to move backward. Only one unlocking button is needed, and the structure is simple. Obviously, two unlocking buttons may also be arranged, one connected to the unlocking pin and the other directly connected to the unlocking press plate, and the unlocking pin and the unlocking press plate are respectively driven by the two unlocking buttons.

In the above example, the ejector plate pin is on the left, the anvil pin is on the right, the limiting button is on the left, and the unlocking button is on the right, which is merely an example. The positions of the ejector plate pin, the anvil pin, the limiting button and the unlocking button may be adjusted, and the limiting button and unlocking button may also be arranged on the same side, which may be adjusted as needed by those skilled in the art.

The following provides a detailed description of the usage method of the present disclosure.

When the stapler of the present disclosure is in an initial state, the anvil ring 1, the cartridge ring 2 and the ejector plate ring 3 are perpendicular to the corresponding pin bodies; the anvil ring 1, the cartridge ring 2 and the ejector plate ring 3 are all in an open state; the anvil pin lock catch 9, the cartridge pin lock catch 10 and the ejector plate pin lock catch 11 are not locked; the male buckles 901, 1001 and 1101 are separated from the female buckles 902, 1002 and 1102 (as shown in FIG. 20); the unlocking springs 903, 1003 and 1103 are in an original straight state, so that the unlocking columns 904, 1004 and 1104 are in a built-in pop-up state; and the ends of the unlocking columns are in the anvil pin (if the unlocking pin is not arranged in the anvil pin, the ends pass through the anvil pin). The cartridge ring 2 and the ejector plate ring 3 are in contact with each other 4-5 cm away from the anvil ring 1 (as shown in FIG. 9). The unlocking pin 12 is in a retracted state, and the unlocking button 13 is in the middle position of the unlocking button moving slot 1904. The limiting button 4 is fixed to the near-end of the limiting button moving slot 1903 by a safety catch (not shown in the figure), and the limiting button end convex block 403 of the limiting button 4 rests against a pushing surface 1603 of the cartridge pin 16. The drive pin 5 can drive both the cartridge pin and the ejector plate pin simultaneously. The reset button 7 is at the near-end of the reset button moving slot 1902, the traction spring pulls the rams 6, the spine 501 below the drive pin 5 is exposed, and the pawl 14 is engaged with the spine 501.

The following is an example of intestinal anastomosis, but the stapler of the present disclosure is not limited to the intestine, and is applicable to any hollow viscera and scenes that can be everted for anastomosis. Excess soft tissue around two broken ends of the intestine is excised, and 2 to 4 traction stitches are sutured at the edges of the broken ends. The stapler in an initial state is taken out, a suitable surgical site for anastomosis is selected, and the male buckles 901, 1001 and 1101 are inserted into the female buckles B902, 1002 and 1102 for locking to form rings. The traction stitch of the broken end at the far-end of the stapler is pulled in from the outside to the inside of the anvil ring 1, and the broken end of the intestine at the far-end is everted and fixed to the inner side of the anvil ring 1. Similarly, the traction stitch of the broken end at the near-end of the stapler is pulled in from the outside to the inside of the ejector plate ring 3 and the cartridge ring 2 sequentially, and the broken end of the intestine at the near-end is everted and fixed to the inner side of the cartridge ring 2. After the two broken ends are aligned in place, the active handle 8 is pulled, the pawl 14 pushes the spine 501 of the drive pin 5 to push the drive pin to move forward, and the drive pin 5 drives the cartridge pin and the ejector plate pin to move forward together. At this point, the ejector plate pin 15 and the cartridge pin 16 respectively drive the ejector plate ring 3, the circular blade 301 and the cartridge ring 2 to move forward, and also drive the broken end of the intestine everted on the cartridge ring to adhere to the broken end of the intestine everted on the anvil ring. In the process of the drive pin driving the cartridge pin and the ejector plate pin forward, when the cartridge pin elastic wings 1601 reach the area of the clamping groove, the two broken ends are close, and the cartridge pin elastic wings 1601 of the cartridge pin are clamped in the clamping groove 1905 of the stapler body. The surgical operator can determine the distance of the cartridge pin 16 driven to move forward based on the thickness of the anastomosed tissue. As the cartridge pin elastic wings 1601 move, one or more continuous "clicks" can be heard until both ends are closely adhered (note: the surgical operator needs to control the tension and pressure of the anastomosed tissue according to the actual scene to prevent tissue necrosis at the anastomotic stoma due to excessive tissue tension or pressure, or insufficient subsequent cutting and anastomosis effect due to excessive distance between the tissues). At this point, the limiting button 4 indicates approaching to the far-end of the limiting button moving slot 1903, and the surgical operator can also determine whether the tissue is in place based on the graduations of the limiting button moving slot 1903. After adhering in place, the active handle 8 is released. After confirming that the periphery of both broken ends of the intestine are between the anvil ring 1 and the cartridge ring 2 and well aligned in place, anastomosis is to be conducted.

If it is found that the tissue between the anvil ring 1 and the cartridge ring 2 is not aligned well or partially detached during the examination of the two broken ends of the intestine before anastomosis, it is necessary to readjust the tissue alignment. The specific operation is to pull the unlocking button 13 back towards the near-end to drive the unlocking pin 12 to move towards the near-end. When the unlocking button 13 is pulled back to a certain range of the corresponding graduations of the unlocking button moving slot 1904, the unlocking pin 12 has driven the unlocking press plate 1201 back to the cartridge pin elastic wings 1601, causing the cartridge pin elastic wings to be compressed. The cartridge pin elastic wings 1601 are no longer clamped in the clamping groove, and the cartridge pin 16 is no longer restricted in movement. At this point, the reset button 7 is pulled back, and the rams 6 are pulled back by the reset button 7 to move backwards and downwards. The rams 6 push down the pawl 14 and covers the spine 501 below the drive pin 5, and the pawl is no longer engaged with the spine 501. The reset button 7 is further pulled back to drive the drive pin 5 back, and the drive pin 5 drives the ejector plate pin 15 and the cartridge pin 16, thereby driving the ejector plate ring 3 and the cartridge ring 2 to move towards the near-end to an appropriate position. The alignment of the tissue between the anvil ring 1 and the cartridge ring 2 is adjusted. The two broken ends are perfectly aligned in place. When the unlocking button 13 is released, the unlocking pin 12 returns to the original position under the action of the second unlocking spring 1206 (at this time, the unlocking pin drives the unlocking press plate to move forward, and the unlocking press plate is detached from the cartridge pin elastic wings. If the second unlocking spring is not arranged, the unlocking button 13 needs to be manually pushed forward, and the unlocking press plate is driven to detach from the cartridge pin elastic wings by the unlocking pin.). Then the active handle 8 is pulled until the tissues at the two broken ends adhere in place for anastomosis.

In the state ready for anastomosis, the cartridge ring rests against the anvil ring, and the cartridge ring cannot be moved anymore (at the same time, the cartridge pin elastic wings are clamped in the clamping groove, the cartridge pin is very stable, the anvil ring 1 and the cartridge ring 2 are kept fixed in the relative position, and the tissues at the aligned two broken ends cannot loosen). The safety catch is pulled out and the limiting button 4 is pushed inward to disengage the limiting button end convex block 403 from the pushing surface 1603 of the cartridge pin. At this point, the drive pin disengages from the cartridge pin and cannot drive the cartridge pin forward when moving forward. Then the active handle 8 is pulled, and the drive pin 5 drives the ejector plate pin 15 to move forward. The ejector plate pin 15 drives the ejector plate ring 3 and the circular blade 301 to move forward. At this point, the ejector ring protecting plate 302 ensures that the two half rings of the ejector plate ring 3 are in the same plane, and enhances the strength of the anastomosis. The ejector plate on the ejector plate ring pushes an anastomotic nail to move towards the anvil ring 1 and punctures the tissue, and thus the anastomotic nail is used for shaping. The anvil protecting plate 101 ensures that the two half rings of the anvil ring 1 are in the same plane and enhances the strength of the anastomosis (as shown in FIG. 28). The circular blade 301 excises excess tissue around the anastomotic stoma.

The active handle 8 is released, and the unlocking button 13 is pushed forward to drive the unlocking pin 12 to move forward. The unlocking pin 12 compresses the unlocking columns 904, 1004 and 1104, and the unlocking columns compress the male buckles 901, 1001 and 1101 to separate from the female buckles 902, 1002 and 1102, thereby opening the anvil ring, the cartridge ring and the ejector plate ring. By manually rotating the rotatable half rings of the anvil ring 1, the cartridge ring 2 and the ejector plate ring 3, the anvil ring, the cartridge ring and the ejector plate ring can be easily moved away from the connected intestine, and the stapler can be taken out from the anastomotic stoma to complete the cutting and anastomosis.

What is claimed is:

1. A stapler, comprising a shell, as well as an ejector plate rod, a cartridge rod, an anvil rod, an unlocking rod, an ejector plate ring, a cartridge ring and an anvil ring, wherein the cartridge rod is between the ejector plate rod and the anvil rod; the ejector plate ring, the cartridge ring and the anvil ring all comprise a first half ring and a second half ring;

hinged ends of the first half rings and the second half rings are rotatably connected, and fixed ends of the second half rings of the ejector plate ring, the cartridge ring and the anvil ring are connected to the front ends of the ejector plate rod, the cartridge rod and the anvil rod, respectively; the rear end of the anvil rod is fixedly installed in the shell, and the rear ends of the ejector plate rod and the cartridge rod are movably installed in the shell and move back and forth along the length direction of the rod bodies of the ejector plate rod and the cartridge rod; and the ejector plate ring, the cartridge ring and the anvil ring are all provided with lock catches for locking the free ends of the first half rings to the fixed ends of the second half rings, and when the unlocking rod is pushed forward along the length direction of the rod body of the unlocking rod, the unlocking rod opens the lock catches.

2. The stapler according to claim 1, wherein the lock catches comprise male buckles and female buckles, the male buckles are arranged on the free ends of the first half rings, the female buckles are arranged on the fixed ends of the second half rings, and circular structures are formed when the male buckles are locked with the female buckles; unlocking columns perpendicular to the length direction of the rod body are arranged in the second half rings;

the unlocking rod is on the outer side of the anvil rod, the unlocking columns of the ejector plate ring, the cartridge ring and the anvil ring pass through and extend out of the anvil rod respectively, or the unlocking rod is arranged in the anvil rod, and the rear end of the unlocking rod is arranged outside the anvil rod, and the unlocking columns of the ejector plate ring, the cartridge ring and the anvil ring extend into the anvil rod respectively; the cartridge rod is provided with an avoidance slot for the unlocking column of the ejector plate rod to move along the length direction of the rod body, and the anvil rod is provided with an avoidance slot for the unlocking columns of the ejector plate rod and the cartridge rod to move along the length direction of the rod body; and when the unlocking rod is pushed forward, the unlocking rod pushes the unlocking columns to move away from the anvil rod, thereby unlocking the male buckles and female buckles through the unlocking columns.

3. The stapler according to claim 2, wherein the male buckles are elastic arms, the female buckles are grooves, and the unlocking columns push the elastic arms out of the grooves to achieve unlocking.

4. The stapler according to claim 2, wherein the free ends of the first half rings are provided with male buckle grooves, the male buckles are spheres arranged in the male buckle grooves through expansion springs, the female buckles are grooves, and the unlocking columns push the spheres out of the grooves to achieve unlocking.

5. The stapler according to claim 2, wherein both the male buckles and the female buckles are hook-shaped, the hook-shaped male buckles and the hook-shaped female buckles are hooked to achieve locking, and the unlocking columns push the hook-shaped female buckles to achieve unlocking.

6. The stapler according to claim 2, wherein the unlocking columns are sheathed with unlocking springs.

7. The stapler according to claim 1, wherein a drive rod that moves back and forth is arranged in the shell, and the drive rod is connected to the rear end of the ejector plate rod; the front end of the drive rod is a double fork arm structure, the rear end of the cartridge rod is provided with a cartridge rod rear end protrusion, the cartridge rod rear end protrusion is in an accommodation cavity of the double fork arm structure, and the body of the cartridge rod penetrates from the gap between an upper extension and a lower extension of the double fork arm structure; the shell is also provided with a limiting button moving slot extending along the length direction of the rod body and a limiting button passing through the limiting button moving slot; the limiting button is provided with a limiting button end block which extends into the accommodation cavity; and the limiting button moves along the length direction thereof, and when the limiting button end block is between the rear wall of the accommodation cavity and the cartridge rod rear end protrusion, the drive rod drives the cartridge rod to move forward.

8. The stapler according to claim 7, wherein the rear end of the ejector plate rod is provided with a ejector plate rod rear end protrusion, the ejector plate rod rear end protrusion is in the accommodation cavity and in contact with the front wall and rear wall of the accommodation cavity, and the body of the ejector plate rod penetrates from the gap between the upper extension and the lower extension of the double fork arm structure; and a through hole for the limiting button to pass through is formed in the ejector plate rod rear end protrusion.

9. The stapler according to claim 7, wherein at the rear end of the cartridge rod, cartridge rod elastic wings are arranged on the cartridge rod, and the cartridge rod elastic wings open towards the rear end; in front of the cartridge rod elastic wings, an unlocking press plate that moves back and forth along the cartridge rod is arranged on the cartridge rod; the front end of the shell is internally provided with a clamping groove that matches the cartridge rod elastic wings; when the unlocking press plate moves to the cartridge rod elastic wings, the cartridge rod elastic wings are retracted; and when the unlocking press plate moves away from the cartridge rod elastic wings towards the far-end, the cartridge rod elastic wings are clamped in the clamping groove.

10. The stapler according to claim 9, wherein the shell is provided with an unlocking button moving slot extending along the length direction of the rod body, and also comprises an unlocking button extending out of the shell from the unlocking button moving slot; and the inner end of the unlocking button is connected to the unlocking press plate.

11. The stapler according to claim 10, wherein the inner end of the unlocking button is connected to the rear end of the unlocking rod, and the unlocking rod is connected to the unlocking press plate.

12. The stapler according to claim 11, further comprising a connecting rod, wherein guide columns are arranged along the length direction of the rod body in the shell, a sliding seat at the rear end of the connecting rod is slidably installed on the guide columns, and the front end of the connecting rod is connected to the rear end of the unlocking rod.

13. The stapler according to claim 12, wherein on both sides of the sliding seat, the guide columns are sheathed with a first unlocking rod spring and a second unlocking rod spring, respectively.

14. The stapler according to claim 9, wherein the cartridge rod elastic wings are arranged on the upper and lower surfaces of the cartridge rod, and the unlocking press plate is a frame or "[" shape.

15. The stapler according to claim 7, wherein a fixed handle is arranged at the rear end of the shell, an active handle is rotatably installed on the fixed handle, and the active handle is in front of the fixed handle; a pawl is rotatably installed at the upper end of the active handle, and the front end of the pawl rests against a spine at the bottom of the drive rod; and a reset button is installed at the rear end of the drive rod, a reset button moving slot extending along the length direction of the drive rod is arranged on the shell, and the reset button passes through the reset button moving slot.

16. The stapler according to claim 1, wherein the shell is provided with an unlocking button moving slot extending along the length direction of the rod body, and also comprises an unlocking button extending out of the shell from the unlocking button moving slot; and the rear end of the unlocking rod is connected to the inner end of the unlocking button.

17. The stapler according to claim 16, further comprising a connecting rod, wherein guide columns are arranged along the length direction of the rod body in the shell, a sliding seat at the rear end of the connecting rod is slidably installed on the guide columns, the front end of the connecting rod is connected to the rear end of the unlocking rod, and the inner end of the unlocking button is connected to the connecting rod.

18. The stapler according to claim 1, wherein an anvil protecting plate is arranged on the outer side of a fixed end of the second half ring of the anvil ring or on the anvil rod, and the anvil protecting plate extends towards a free end of the first half ring of the anvil ring.

19. The stapler according to claim 1, wherein the ejector plate ring is provided with an ejector plate that matches anastomotic nails, and a circular blade is arranged at the outer edge of the ejector plate.

20. The stapler according to claim 1, wherein the cross-sections of the ends of the first half ring and the second half ring are L-shaped.

* * * * *